US012702655B2

(12) United States Patent
Neas et al.

(10) Patent No.: US 12,702,655 B2
(45) Date of Patent: Aug. 11, 2026

(54) ANTIMICROBIAL, DISINFECTING AND WOUND HEALING COMPOSITIONS AND METHODS FOR PRODUCING AND USING SAME

(71) Applicant: Armis Biopharma, Inc., Fort Collins, CO (US)

(72) Inventors: Edwin Neas, Nunn, CO (US); Scott Noblitt, Fort Collins, CO (US)

(73) Assignee: Armis Biopharma, Inc., Fort Collins, CO (US)

(*) Notice: Subject to any disclaimer, the term of this patent is extended or adjusted under 35 U.S.C. 154(b) by 0 days.

(21) Appl. No.: 18/339,096

(22) Filed: Jun. 21, 2023

(65) Prior Publication Data

US 2023/0404962 A1 Dec. 21, 2023

Related U.S. Application Data

(63) Continuation of application No. 16/736,546, filed on Jan. 7, 2020, now abandoned, which is a continuation-in-part of application No. PCT/US2018/041163, filed on Jul. 7, 2018.

(60) Provisional application No. 62/530,045, filed on Jul. 7, 2017.

(51) Int. Cl.

| | |
|---|---|
| ***A61K 31/327*** | (2006.01) |
| ***A61K 9/00*** | (2006.01) |
| ***A61K 33/06*** | (2006.01) |
| ***A61P 17/02*** | (2006.01) |

(52) U.S. Cl.

CPC .......... *A61K 31/327* (2013.01); *A61K 9/0014* (2013.01); *A61K 33/06* (2013.01); *A61P 17/02* (2018.01)

(58) Field of Classification Search

CPC .. A61K 31/327; A61K 2300/00; A61K 33/40; A61P 17/02

See application file for complete search history.

(56) References Cited

U.S. PATENT DOCUMENTS

| | | | |
|---|---|---|---|
| 2,609,391 | A | 9/1952 | Greenspan et al. |
| 3,009,468 | A | 11/1961 | Eberle |
| 3,365,487 | A | 1/1968 | Gonse |
| 4,385,008 | A | 5/1983 | Hignett |
| 4,403,994 | A | 9/1983 | Hignett |
| 4,483,781 | A | 11/1984 | Hartman |
| 5,055,287 | A | 10/1991 | Kessler |
| 5,296,239 | A | 3/1994 | Colery et al. |
| 5,508,046 | A | 4/1996 | Cosentino et al. |
| 6,369,288 | B1 | 4/2002 | Brown |
| 6,482,786 | B1 | 11/2002 | Del Duca et al. |
| 6,491,896 | B1 | 12/2002 | Rajaiah et al. |
| 6,492,443 | B1 | 12/2002 | Kodemura et al. |
| 7,494,950 | B2 | 2/2009 | Armitage et al. |
| 7,628,851 | B2 | 12/2009 | Armitage et al. |
| 8,057,595 | B2 | 11/2011 | Armitage et al. |
| 9,044,527 | B2 | 6/2015 | Neas et al. |
| 9,283,202 | B2 | 3/2016 | Neas et al. |
| 9,427,417 | B2 | 8/2016 | Myntti |
| 9,844,219 | B2 | 12/2017 | Neas et al. |
| 9,877,483 | B2 | 1/2018 | Neas et al. |
| 11,006,629 | B2 | 5/2021 | Neas et al. |
| 11,284,621 | B2 | 3/2022 | Neas et al. |
| 12,232,962 | B2 | 2/2025 | Noblitt |
| 2003/0235623 | A1 | 12/2003 | Van Oosterom |
| 2004/0057868 | A1 | 3/2004 | McVey et al. |
| 2005/0153857 | A1 | 7/2005 | Sherry et al. |
| 2005/0197397 | A1 | 9/2005 | Martin |
| 2005/0208094 | A1 | 9/2005 | Armitage et al. |
| 2005/0229344 | A1 | 10/2005 | Mittelstaedt et al. |
| 2007/0048175 | A1 | 3/2007 | Tichy et al. |
| 2008/0226691 | A1 | 9/2008 | Armitage et al. |
| 2009/0061017 | A1 | 3/2009 | Pedersen et al. |
| 2009/0144925 | A1 | 6/2009 | Orffeo |
| 2009/0311198 | A1 | 12/2009 | Concar et al. |
| 2010/0016322 | A1 | 1/2010 | Nagaraju et al. |
| 2010/0021558 | A1 | 1/2010 | Dada et al. |
| 2010/0048763 | A1 | 2/2010 | Armitage et al. |
| 2010/0108942 | A1 | 5/2010 | Man et al. |
| 2011/0232018 | A1 | 9/2011 | Mans et al. |
| 2012/0207806 | A1 | 8/2012 | LoPesio |
| 2012/0213835 | A1 | 8/2012 | Neas et al. |
| 2013/0018097 | A1 | 1/2013 | Bolduc et al. |
| 2013/0072563 | A1* | 3/2013 | Ho ........................ A61L 2/22 514/557 |
| 2013/0251590 | A1 | 9/2013 | Golden et al. |

(Continued)

FOREIGN PATENT DOCUMENTS

| | | | |
|---|---|---|---|
| CN | 103843817 | A | 6/2014 |
| DE | 202015001904 | U1 | 5/2015 |

(Continued)

OTHER PUBLICATIONS

Nagoba et al (Journal of Infection and Public Health, 2013, vol. 6, pp. 410-415) (Year: 2013).*

Turcic et al (Acta Med Croatica 51:159-162, 1997) (Year: 1997).*

Lim et al., "Normal saline wound dressing—is it really normal?", British Journal of Plastic Surgery (2000), 53: 42-45.

Wagner et al., "Formulation of a Broad-Spectrum, All-Weather, Solid-Based, Peracetate—'Solvent' Dry Decontaminant Concentrate," Edgewood Chemical Biological Center Aberdeen Proving Ground MD Research and Technolgy Dir (2010), (42 pp) retreived at URL: https://apps.dtic.mil/sti/pdfs/ADA520685.pdf.

Dittmar et al., "The Influence of Certain Inorganic Salts of the Germicidal Activity of Hydrogen Peroxide," J. Bacteriology (1930), 19(3): 203-11.

(Continued)

*Primary Examiner* — Craig D Ricci

(74) *Attorney, Agent, or Firm* — Fox Rothschild LLP

(57) ABSTRACT

The present invention relates to antimicrobial, disinfecting, and wound healing compositions and methods for producing and using the same. The compositions may comprise one or more of a peracid, a hydroperoxide, a bis(hydroperoxide), or an epoxide.

6 Claims, 11 Drawing Sheets

(56) References Cited

U.S. PATENT DOCUMENTS

2013/0330397 A1* 12/2013 Neas .................. A61L 26/0066 525/453
2014/0113000 A1* 4/2014 Neas ..................... A01N 59/00 514/475
2014/0120179 A1 5/2014 Smith et al.
2014/0249140 A1 9/2014 Niquet et al.
2014/0287154 A1 9/2014 Kaiser et al.
2015/0093425 A1 4/2015 Moore
2015/0133359 A1 5/2015 Molnar et al.
2015/0196526 A1 7/2015 Neas et al.
2015/0291520 A1 10/2015 Reinold et al.
2016/0174553 A1 6/2016 Matta et al.
2017/0100335 A1 4/2017 Hemmila et al.
2017/0118991 A1 5/2017 Neas et al.
2017/0303538 A1* 10/2017 Neas .................... C07C 409/24
2018/0235231 A1 8/2018 Ahmadpour et al.
2019/0021330 A1 1/2019 Neas et al.
2020/0129383 A1 4/2020 Neas et al.
2020/0246511 A1 8/2020 Noblitt
2020/0276149 A1 9/2020 Neas et al.
2021/0077438 A1 3/2021 Noblitt et al.
2021/0093602 A1 4/2021 D'Agostino et al.
2021/0337794 A1 11/2021 Neas et al.
2022/0023174 A1 1/2022 Noblitt et al.
2022/0030871 A1 2/2022 Bui et al.
2022/0226086 A1 7/2022 Noblitt et al.

FOREIGN PATENT DOCUMENTS

EP 0105689 A2 4/1984
EP 1070505 A1 1/2001
EP 0873687 B1 6/2002
EP 2662330 A1 * 11/2013 ........... C01B 15/037
EP 2965624 A1 1/2016
EP 2398508 B1 5/2016
EP 1663333 B1 11/2018
EP 2885046 B1 8/2019
FR 2796286 B1 6/2002
GB 1041983 A 9/1966
GB 2278057 A 11/1994
JP 60163902 A 8/1985
JP 2001-199811 A 7/2001
JP 2007-520479 A 7/2007
JP 2010526816 A 8/2010
JP 2010537970 A 12/2010
JP 5332679 B2 11/2013
WO 1993001822 A1 2/1993
WO 200233038 A2 4/2002
WO 2004020562 A1 3/2004
WO 2010049892 A2 5/2010
WO 2012128629 A1 9/2012
WO 2014028633 A1 2/2014
WO 2016100818 A1 6/2016
WO 2019010465 A1 1/2019
WO 2019010467 A2 1/2019
WO 2020069079 A1 4/2020
WO 2020252402 A1 12/2020
WO 2021142148 A1 7/2021
WO 2021142152 A1 7/2021

OTHER PUBLICATIONS

Baldry, "The bactericidal, fungicidal and sporicidal properties of hydrogen peroxide and peracetic acid," J Applied Bacteriology (1982), 54: 417-23.
Madronich, S., "Chemical Evolution of Gaseous Air Pollutants Down-Wind of Tropical Megacities: Mexico City Case Study" Atmospheric Environment, 2006, vol. 40, pp. 6012-6018.
Jacks et al., "Evaluation of Peracid Formation as the Basis for Resistance to Infection in Plants Transformed with Haloperoxidase", Journal of Agricultural and Food Chemistry, 2002, 50: 706-709 (see abstract).
Davies et al., "A convenient preparation of aqueous methyl hydroperoxide and a comparison of its reactivity towards triacetylethylenediamine with that of other nucleophiles: the mechanism of peroxide bleach activation", Journal of Chemical Society, Perkin Transactions 2, 1992, pp. 559-562.
International Search Report and Written Opinion issued Sep. 24, 2018, in Application No. PCT/US2018/041163 (9 pages).
International Search Report and Written Opinion issued Mar. 26, 2021, in Application No. PCT/US2021/012536 (8 pages).
International Search Report and Written Opinion issued Mar. 26, 2021, in Application No. PCT/US2021/012540 (8 pages).
International Search Report and Written Opinion issued Sep. 9, 2020, in Application No. PCT/US2020/037616 (14 pages).
Information about Related Patents and Patent Applications, see section 4 of the accompanying Information Disclosure Statement Letter, which concerns Related Patents and Patent Applications.
Extended European Search Report issued Mar. 16, 2021 in Application No. 18828616.5 (8 pages).
Osovsky et al., "Decontamination of Adsorbed Chemical Warfare Agents on Activated Carbon Using Hydrogen Peroxide Solutions", Environmental Sci and Tech (2014), 48:10912-10918.
Alarcon et al., "Antimocrobial properties of magnesium chloride at low pH in the presence of anionic bases", Magnes Res (2014), 27:57-68 (Abstract only).

* cited by examiner

$H_2O_2$ bis(hydroperoxide)

| Decon | N | 24 hr Probit Estimates | | | Est. PR[1] |
|---|---|---|---|---|---|
| | | $LD_{50}$ µg/kg, p.c. | Delta 95% CI | Slope | |
| 2% Composition | 26 | 5959 | 4858-7309 | 6.4 | 42.6 |
| RSDL | 15 | 3380 | 2921-3910 | 12.7 | 24.1 |

1. Estimated using 140 ug/kg in denominator of the Protective Ratio (PR)

| Decon | N | 24 hr Probit Estimates | | | Est. PR[1] |
|---|---|---|---|---|---|
| | | $LD_{50}$ µg/kg, p.c. | Delta 95% CI | Slope | |
| Water | 25 | 3198 | 2760 - 3706 | 12.1 | 23 |
| 1% Dawn™ Det. | 29 | 3622 | 2926 - 4484 | 7.4 | 26 |
| RSDL-G[2] | 37 | 5287 | 4792 -5832 | 11.4 | 38 |
| RSDL-S[3] | 25 | 6912 | 5920 -8070 | 11.0 | 49 |
| 2% Composition | 41 | 15160 | 14209-16174 | 20.8 | 108 |

1. Estimated using 140 µg/kg in the denominator of the Protective Ratio (PR)
2. Applied with gauze
3. Applied with commercial sponge pad

ANTIMICROBIAL, DISINFECTING AND WOUND HEALING COMPOSITIONS AND METHODS FOR PRODUCING AND USING SAME

CROSS-REFERENCE TO RELATED APPLICATION

The application is a Continuation of U.S. patent application Ser. No. 16/736,546, filed Jan. 7, 2020, which is a Continuation-In-Part of International Patent Application No. PCT/US2018/041163, filed Jul. 7, 2018, which claims priority under 35 U.S.C. § 119(e) to U.S. Provisional Application Ser. No. 62/530,045 filed July 7. 2017, the disclosures of which are incorporated by reference herein in their entireties.

FIELD OF THE INVENTION

The present invention relates to antimicrobial, disinfecting, and wound healing compositions and methods for producing and using the same. The compositions may comprise one or more of a peracid, a hydroperoxide, a bis (hydroperoxide), or an epoxide.

BACKGROUND OF THE INVENTION

The skin is the body's largest organ and serves as the primary protective barrier to the outside world. Any physical disruption (i.e., wound) to this organ must therefore be quickly and efficiently repaired in order to restore tissue integrity and function. Quite often proper wound healing is impaired with devastating consequences such as severe morbidity, amputations, or death. In humans and animals, protection from mechanical injury, chemical hazards, and bacterial invasion is provided by the skin because the epidermis is relatively thick and covered with keratin. Secretions from sebaceous glands and sweat glands also benefit this protective barrier. In the event of an injury that damages the skin's protective barrier, the body triggers a wound healing cascade of events.

The classical model of wound healing is divided into three or four sequential, yet overlapping, phases: (1) hemostasis, (2) inflammatory, (3) proliferative and (4) remodeling. The hemostasis phase involves platelets (thromboctytes) to form a fibrin clot to control active bleeding. The inflammatory phase involves migration of phagocytes to the wound to kill microorganisms and release of subsequent signaling factors to involve the migration and division of cells involved in the proliferative phase. The proliferative phase involves vascular cell production for angiogenesis, fibroblast cells to excrete collagen and fibronectin to form an extracellular matrix, and epithelial cells to reform the external epidermis. In addition, the wound is made smaller by myofibroblasts. Finally, collagen is remodeled and cells that are no longer needed are removed by programmed cell death (i.e., apoptosis).

The process of wound healing can be divided into two major phases: early phase and cellular phase. See FIG. 1. The early phase involves hemostasis which involves vasoconstriction, temporary blockage of a break by a platelet plug, and blood coagulation, or formation of a clot that seals the hole until tissues are repaired. The early phase also involves the generation of stimuli to attract the cellular responses needed to instigate inflammation. In the inflammation phase, white blood cells, or leukocytes, are attracted to the wound site by platelet-derived growth factor (PDGF), and these cells of the immune system are involved in defending the body against both infectious disease and foreign materials.

There are 18 other known proteins involved in the inflammatory phase which interact to regulate this response. For example, IL-4, IL-10, and IL-13 are potent activators of B lymphocytes. However, IL-4, IL-10, and IL-13 are also potent anti-inflammatory agents. The phagocytic cells engulf and then digest cellular debris and pathogens and stimulate lymphocytes and other immune cells to respond to the wound area. Once the invading microorganisms have been brought under control, the skin proceeds through the proliferative and remodeling stage by a complex cascade of biochemical events orchestrated to repair the damage. This involves the formation of a scab within several hours. The scab temporarily restores the integrity of the epidermis and restricts the entry of microorganisms.

After the scab is formed, cells of the stratum basale begin to divide by mitosis and migrate to the edges of the scab. A week after the injury, the edges of the wound are pulled together by contraction. Contraction is an important part of the healing process when damage has been extensive, and involves shrinking in size of underlying contractile connective tissue, which brings the wound margins toward one another. In a major injury, if epithelial cell migration and tissue contraction cannot cover the wound, suturing the edges of the injured skin together, or even replacement of lost skin with skin grafts, may be required to restore the skin. Interruption of this healing process by a breakdown in any of these wound healing processes will lead to a chronic wound.

Other skin wounds involve burns. Major burns are relatively common injuries that require multidisciplinary treatment for patient survival and recovery. More than 30,000 people die each year worldwide because of fire-related burn injuries. Many more are seriously injured, disabled, or disfigured because of all types of burns. There have been significant advances in medical care for burns over the last 15 years due to fluid resuscitation, wound cleaning, skin replacement, infection control, and nutritional support. These changes have primarily resulted from the use of early burn wound excursion, early adequate nutrition, and the use of surgical techniques that minimize blood and heat loss. Since modern treatment of burns has greatly advanced, sepsis has become the leading cause of death after a burn injury. Multiple antibiotic resistant bacteria and fungus now account for the bulk of deaths due to sepsis in burns, the etiology of which is due to antibiotic resistant bacteria and biofilm formation in the wound and extraneous nosocomial infections.

Impediments to wound healing include hypoxia, infection, presence of debris and necrotic tissue, use of inflammatory medications, a diet deficient in vitamins or minerals or general nutrition, tumors, environmental factors, and metabolic disorders such as diabetes mellitus. The primary impediments to acute wound healing are hypoxia, infection, wound debris, and anti-inflammatory medications. The molecular events in the wound healing process of acute, chronic and burn wounds continues to be studied and exhibits an extremely complex array of biochemical events imposing a regulated cascade of inter and intra cellular events.

A rapidly growing field of wound healing research is centered around cellular growth factors and the use of these factors for the treatment of wounds. The biochemical response at the cellular level is a process involving intricate interactions among different cell functions which include energy production, structural proteins, growth factors, and proteinases. The treatment of wounds with known cellular growth factors has the potential ability to help heal wounds by stimulating the cellular processes involved in angiogenesis, cellular proliferation, regulating the production and degradation of the extracellular matrix, and being the signal for attracting the inflammatory cells and fibroblasts. Obviously, this complexity requires a plethora of biochemical reactions to provide the functions necessary to accomplish healing of the wound and is not completely understood at this point.

One emerging area of research is the metabolic effect of the alpha keto acids on wound healing. U.S. Pat. No. 6,329,343 discloses the use of a composition of salts of pyruvic acid and/or salts of pyruvic acid and alpha keto glutaric acid, a mixture of fatty acids, and an effective amount of an antibacterial agent as a bioadhesive antibacterial wound healing composition.

Several strategies have been employed to combat the significant infectious complication rates associated with wounds. However, to-date, these strategies have been mainly limited to improved surgical asepsis, surgical technique, and administrative regimens of peri-operative systemic antibiotics and local antibiotic irrigation procedures which have not been well defined. New approaches are emerging in the clinic, including vacuum-sealed dressings, transparent film dressings, irrigation with antimicrobial agents, use of the port and cap, use of new agents such as deuteroporphyrin, gamma interferon (IFN-y), silver sulfadiazone water soluble gel, geomagnetic therapy, and natural remedies such as milliacynic oil and lysozyme.

Unfortunately, few of these innovations have made a major impact on infection and fatality rates and have been shown to have cellular toxicity issues. Most new approaches involve delivery of antimicrobial compounds, to which many wound pathogens are resistant, in some form of salve or in dressings. These treatments lend themselves to continued production of antibiotic resistant bacteria which will negatively affect future therapies against resistive bacteria such as Methicillin-Resistant *Staphylococcus aureus* (MRSA), Vancomycin-resistant enterococci (VRE) and *Acinetobacter baumanni. A baumannii* accounts for 6% of Gram-negative infections in intensive care facilities in the USA, with mortality rates as high as 54% having been reported. Isolation of MDR *Acinetobacter* soared from 6.7% in 1993 to 29.9% by 2004, emphasizing the need for newer and better drugs. Out of 1,040 antibiotics tested only 20 (1.92%) exhibited significant antimicrobial activity and only five compounds exhibited activity against the more resistant BAA-1605 A *baumanni.*

Today, MRSA and *C. difficile* are the leading causes of nosocomial infection in most parts of the world. In 2003, *S. aureus* was the leading pathogen associated with skin and soft tissue infections. In the last 20 years, MRSA has moved from an exclusively hospital-acquired pathogen (HA-MRSA) to another type known as a community-acquired pathogen, CA-MRSA. In fact, it has been stated that topical application of antibiotic solutions for lower-limb open fracture wounds offers no advantage over the use of a nonsterile soap and may increase the risk of wound-healing problems.

Wound healing and "good" care of wounds has been synonymous with topical prevention and management of microbial contamination. Today's primary therapy involves the use of either topical application of antiseptics or systemic and topical use of antibiotics. The general perspective is that topical application of antibiotics to wounds has no advantages over the use of other antiseptic methods and may increase the risk of wound-healing by producing a sovereign bacteria that is resistant within the wound. The use of silver-based dressings for therapy against infections are widely used in chronic wound and burn therapy. There are several of these commercially available such as Acticoatt™, Aquacels Age, Contreet® Foam, PolyMem® Silver, Urgotul® SSD). These silver containing dressings do not kill spores or biofilms and require long exposure times that may become cytotoxic over time. The major cause of sepsis in burn wounds, *Aspergillus niger* has a 70% fatality and is not susceptible to silver compounds.

The cytotoxic effect would explain, in part, the clinical observation of delayed wound healing or inhibition of wound epithelialization after the use of certain topical silver dressings.

There are a myriad of solutions available that claim to kill 99.9% of MRSA and other vegetative bacteria and some spores on surfaces and skin (e.g., hand sanitizers). Therefore, these solutions leave one viable bacterium, or spore, in a thousand or a thousand viable bacteria, or spores, in a million after treatment. However, contaminated surfaces can contain millions of bacteria, some of which can be contained within complex matrices such as blood drops, thus making them difficult to kill. Other types of bacteria, such as *Bacillus subtilis*, form biofilms on surfaces of endoscopes and other medical devices for insertion into the body, which affects the kill efficacy of most disinfectants. These low level disinfectants, often called sanitizers, that claim to kill 99.9% of the bacteria present will not completely kill all bacteria which are present in higher populations (colonized), contained within a complex matrix, or existing as a biofilm.

There are currently several topical antiseptics on the market that are used to diminish the growth of bacterial infections in wounds. Most antiseptics are not suitable for open wounds because they may impede wound healing by direct cytotoxic effects to keratinocytes and fibroblasts. In general, current topical antiseptics have limited bactericidal effect (e.g., 3 log reduction in 30 minute exposure) and nearly all have some cytotoxicity effect which varies with concentration and application time.

There are primarily five high level disinfectants/sterilants in use today. These include glutaraldehyde, orthophthalaldehyde, hypochlorite, hydrogen peroxide, and peracetic acid. The aldehydes are highly toxic and take a very long time to affect a >99.9999% (or 6 log kill). The most successful high level disinfectants used today are oxidizers such as hypochlorites, hydrogen peroxide and peracetic acid. The reactive advantage for disinfection by oxidation is the nonspecific free radical damage to all components of the microbe, including proteins, lipids, and DNA. Therefore, microbial resistance to oxidation at high enough solution concentration is virtually non-existent.

Safe and non-toxic concentrations of hydrogen peroxide are not capable of killing spores or high populations of microbes. Hypochlorous acid, which is formed by PMN by myeloperoxidase-mediated peroxidation of chloride ions, is easily neutralized at physiological pH by nitrite, a major end-product of cellular nitric oxide (NO) metabolism, and its bactericidal effects subsequently diminished and it is not as effective as silver sulfadiazine, a common topical wound sanitizer.

However, it appears that hypochlorous acid does not inhibit wound healing at the concentrations for the effective biocidal levels used. That may be because it is a natural compound found in the inflammatory phase of wound healing. Peracetic acid is used mainly in the food industry, where it is applied as a cleanser and as a disinfectant. Since the early 1950's, acetic acid was applied for bacteria and fungi removal from fruits and vegetables. It was also used for the disinfection of recycled rinsing water for foodstuffs. Nowadays peracetic acid is applied for the disinfection of medical supplies and to prevent biofilm formation in pulp industries. It can be applied during water purification as a disinfectant and for plumbing disinfection. Peracetic acid is produced by a reaction between hydrogen peroxide and acetic acid or it can also be produced by oxidation of acethaldehyde. Peracetic acid is a very powerful oxidant; the oxidation potential outranges that of chlorine and chlorine dioxide. Peracetic acid has not been tested in wound healing. However, it is not known to be involved in any significant cellular metabolism and is typically produced with toxic sulfuric acid catalyst. Thus, many conventional topical wound sanitizers have various limitations.

s stated above, a drawback of the peroxyacid-based chemical disinfectants is their inherent lack of stability, which poses a challenge for shelf-life when used for long term applications. Thus, a need exists for a peracid-based disinfectant, which is an effective broad spectrum antimicrobial, is in an easily removable homogenous antimicrobial coating composition providing both short-term and extended long-term antimicrobial efficacy after application to a surface or a wound.

In addition, there is a continuing need for new topical wound sanitizers, healers or both, and in particular there is a need to develop peroxyacids that are effective sporocides, bactericids and virucides for wounds which are easy to handle and store. Moreover, there is a need for peroxyacids that are easy to handle and store and that have a low corrosive nature. It is therefore desirable to develop a sanitizer that does not decompose rapidly and violently and that can be used as a topical wound sanitizer or as an antimicrobial coating.

The present invention is directed toward overcoming one or more of the problems discussed above.

SUMMARY OF THE INVENTION

In some aspects, the present invention relates to novel antimicrobial, disinfecting, and/or wound healing compositions and methods for producing and using the same. The compositions may comprise one or more of a keto acid, a peroxyacid, a hydroperoxide, a bis (hydroperoxide), or an epoxide.

In one aspect, the present invention provides a wound healing composition made by a method comprising contacting a keto acid or a salt or anhydride thereof with an oxidizing agent while stirring and under conditions sufficient to produce one or more of a peroxyacid, a hydroperoxide, a bis(hydroperoxide), or an epoxide. In some embodiments, the conditions are sufficient to produce a peroxyacid and a bis(hydroperoxide). In some embodiments, the conditions are sufficient to produce a peroxyacid, a hydroperoxide, a bis(hydroperoxide), and an epoxide.

In some embodiments, the keto acid may be an alpha-, beta-, or gamma-keto acid. In other embodiments, the keto acid is an alpha-keto acid. In some embodiments, the keto acid is pyruvic acid or a salt or anhydride thereof. In other embodiments, the keto acid is parapyruvuc acid or a salt or anhydride thereof. In other embodiments, the keto acid is acetoacetic acid or a salt or anhydride thereof. In some embodiments, the keto acid salt may be a lithium, sodium, potassium, rubidium, cesium, zinc, magnesium, or calcium salt, or a mixture thereof. In other embodiments, the process further comprises contacting the keto acid or salt thereof and the oxidizing agent with maleic acid or anhydride, citraconic acid or anhydride, or a mixture thereof.

In some embodiments, the reaction temperature is about 10° C. or less. In other embodiments, the reaction temperature ranges from about −10° C. to 10° C. In some embodiments, the molar ratio of oxidizing agent to keto acid typically ranges from 1:1 to about 4:1.

In one embodiment, the method comprises stirring the oxidizing agent at a shear rate between 150 $s^{-1}$ and 850 $s^{-1}$, cooling the oxidizing agent to between −10° C. to 0° C., and adding the keto acid at a rate sufficient to maintain the temperature between −10° C. to 0° C. during addition of the keto acid to form a reaction solution. A shear rate between about 150 and about 850 $sec^{-1}$ equates to stirring at a rate between about 90 and about 500 RPM. In some embodiments, the method further comprises continually stirring the reaction solution for 10 to 12 hours at a temperature −10° C. to 0° C. In other embodiments, the method further comprises warming the reaction solution to between 14° C. and 27° C. In some embodiments, the method further comprises cooling the reaction solution to maintain this temperature for 30 days. In some embodiments, the oxidizing agent is hydrogen peroxide and the keto acid is pyruvic acid.

In another aspect, the present invention provides a wound healing composition made by a method comprising contacting citramalic acid or a salt thereof with an oxidizing agent while stirring under conditions sufficient to produce one or more of a peroxyacid, a hydroperoxide, a bis(hydroperoxide), or an epoxide. In some embodiments, the conditions are sufficient to produce a peroxyacid, a hydroperoxide, a bis (hydroperoxide), and an epoxide. In some embodiments, the citramalic acid salt may be a lithium, sodium, potassium, rubidium, cesium, zinc, magnesium, or calcium salt, or a mixture thereof. In other embodiments, the process further comprises contacting citramalic acid or salt thereof and the oxidizing agent with acetic acid or anhydride thereof, maleic acid or anhydride thereof, citraconic acid or anhydride thereof, or a mixture thereof.

In another aspect, the present invention provides a wound healing composition made by a method comprising contacting an acetoacetate ester or a salt thereof with an oxidizing agent while stirring under conditions sufficient to produce one or more of a peroxyacid, a hydroperoxide, a bis(hydroperoxide), or an epoxide. In some embodiments, the conditions are sufficient to produce a peroxyacid, a hydroperoxide, a bis(hydroperoxide), and an epoxide. In some embodiments, the acetoacetate ester may be methyl acetoacetate or ethylacetoacetate, or a mixture thereof. In other embodiments, the acetoacetate ester salt may be a lithium, sodium, potassium, rubidium, cesium, zinc, magnesium, or calcium salt, or a mixture thereof. In some embodiments, the process further comprises adding citramalic acid.

While a variety of oxidizing agents may be used in such methods, typical oxidizing agents may comprise hydrogen peroxide, barium peroxide, sodium carbonate peroxide, potassium superoxide, or a mixture thereof. In some embodiments, the oxidizing agent is hydrogen peroxide.

In another aspect, the present invention provides a wound healing composition comprising a peroxyacid and a bis (hydroperoxide). In some embodiments, the composition further comprises a hydroperoxide. In other embodiments, the composition further comprises an epoxide. In some embodiments, the composition comprises peracetic acid and 3,3-bis(hydroperoxy) butanoic acid. In other embodiments, the composition comprises peracetic acid and 3,3-bis(hydroperoxy) butaneperoxoic acid. In other embodiments, the composition further comprises at least one of methylhydroperoxide and hydroxymethyl hydroperoxide. In some embodiments, the composition further comprises 5-hydroperoxy-5-methyl-1,2-diox-olan-3-one. In some embodiments, the composition further comprises hydrogen peroxide.

In some embodiments, the wound healing composition further comprises peroxycitraconic acid. The peroxycitraconic acid may be either (2Z)-4-hydroperoxy-3-methyl-4-oxobut-2-enoic acid, (2Z)-4-hydroperoxy-2-methyl-4-oxobut-2-enoic acid, or a mixture thereof. In other embodiments, the compositions may comprise diperoxycitraconic acid, i.e., (2Z)-2 -methylbut-2-enediperoxoic acid. In other embodiments, the composition further comprises peroxycitramalic acid. The peroxycitramalic acid may be either 4-hydro-peroxy-2-hydroxy-2-methyl-4-oxobutanoic acid, 4-hydroperoxy-3-hydroxy-3-methyl-4-oxo-butanoic acid, or a mixture thereof.

In some embodiments, the present invention provides a wound healing composition comprising 3,3-bis(hydroperoxy) butanoic acid, 3,3-bis(hydroperoxy) butaneperoxoic acid, or 3-oxobutaneperoxoic acid, or a mixture thereof. In other embodiments, the compositions further comprise 5-hydroperoxy-5-methyl-1,2-dioxolan-3-one. In some embodiments, the composition further comprises one or more of hydrogen peroxide, an organic hydroperoxide, an organic peroxide, an organic peracid, an inorganic peracid, an organic acid, or an inorganic acid. In some embodiments, the composition further comprises hydrogen peroxide.

In some embodiments, the present invention provides a wound healing composition comprising acetoacetic acid, or a salt of acetoacetic acid. The salt of acetoacetic acid may be a lithium, sodium, potassium, rubidium, cesium, zinc, magnesium, or calcium salt. The composition may further comprise a hydroperoxide, including hydrogen peroxide and/or an organic hydroperoxide. In other embodiments, the composition may further comprise a keto acid. The keto acid may be an alpha-, beta- or gamma-keto acid. In some embodiments, the composition may further comprise pyruvic acid, parapyruvic acid, or citramalic acid, any of their salts, or mixtures thereof. In other embodiments, the composition may further comprise an acetoacetate ester such as methyl acetoacetate, ethyl acetoacetate, or acetoacetic anhydride. In some embodiments, the composition further comprises hydrogen peroxide.

In some embodiments, the present invention provides a wound healing composition comprising hydroperoxyacetic acid. In other embodiments, the composition further comprises hydrogen peroxide.

In another aspect, the present invention provides an antimicrobial, chemical oxidizer, or disinfecting products comprising one or more of the above-described compositions. In some embodiments, the antimicrobial product is a household care product. Within such embodiments, in some cases the house hold care product is selected from the group consisting of hard surface cleaners, deodorizers, fabric care compositions, fabric cleaning compositions, manual dish detergents, automatic dish detergents, floor waxes, kitchen cleaners, bathroom cleaners, and combinations thereof. In other embodiments, the anti-microbial product is selected from the group consisting of hard surface cleaners, deodorizers, fabric care compositions, fabric cleaning compositions, manual dish detergents, automatic dish detergents, floor waxes, kitchen cleaners, bathroom cleaners, and combinations thereof. Antimicrobial products of the invention can be used in a wide variety of settings including, but not limited to, in health care facilities such as hospitals, rehabilitation, assisted living facilities, etc.

In other embodiments, the antimicrobial product is a medical device disinfectant. Still in other embodiments, the antimicrobial product is used as a disinfectant for aseptic filling equipment. Yet in other embodiments, the antimicrobial product is used in an aseptic food processing system. In other embodiments, the antimicrobial product is used as a disinfectant for biofilms in water systems. Still in other embodiments, the antimicrobial product is used as a disinfectant for waste water treatment.

In yet another aspect the present invention provides a method of making a wound healing composition comprising contacting a keto acid or a salt or anhydride thereof with an oxidizing agent while stirring and under conditions sufficient to produce one or more of a peroxyacid, a hydroperoxide, a bis(hydroperoxide), or an epoxide. In some embodiments the conditions are sufficient to produce a peroxyacid, a hydroperoxide, a bis(hydroperoxide), and an epoxide.

In some embodiments, the keto acid may be an alpha-, beta-, or gamma-keto acid. In some embodiments, the keto acid is pyruvic acid or a salt or anhydride thereof. In other embodiments, the keto acid is parapyruvuc acid or a salt or anhydride thereof. In other embodiments, the keto acid is acetoacetic acid or a salt or anhydride thereof. In some embodiments, the keto acid salt may be a lithium, sodium, potassium, rubidium, cesium, zinc, magnesium, or calcium salt, or a mixture thereof. In other embodiments, the process further comprises contacting the keto acid or salt thereof and the oxidizing agent with maleic acid or anhydride, citraconic acid or anhydride, or a mixture thereof.

In some embodiments, the reaction temperature is about 10° C. or less. In other embodiments, the reaction temperature ranges from about −10° C. to 10° C. In some embodiments, the molar ratio of oxidizing agent to keto acid typically ranges from 1:1 to about 4:1. In some embodiments, the stirring is at a shear rate between 150 $s^{-1}$ and 850 $s^{-1}$.

In one embodiment, the method comprises stirring the oxidizing agent at a shear rate between 150 $s^{-1}$ and 850 $s^{-1}$, cooling the oxidizing agent to between −10° C. to 0° C., and adding the keto acid at a rate sufficient to maintain the temperature between −10° C. to 0° C. during addition of the keto acid to form a reaction solution. A shear rate between about 150 and about 850 $sec^{-1}$ equates to stirring at a rate between about 90 and about 500 RPM. In some embodiments, the method further comprises continually stirring the reaction solution for 10 to 12 hours. In other embodiments, the method further comprises warming the reaction solution to between 14° C. and 27° C. In some embodiments, the method further comprises cooling the reaction solution to maintain this temperature for 30 days. In some embodiments the temperature is room temperature (between 20° C. and 22° C.) In some embodiments, the oxidizing agent is hydrogen peroxide and the keto acid is pyruvic acid.

In another aspect, the present invention provides a method of making a wound healing composition comprising contacting citramalic acid or a salt thereof with an oxidizing agent while stirring under conditions sufficient to produce one or more of a peroxyacid, a hydroperoxide, a bis(hydroperoxide), or an epoxide. In some embodiments, the conditions are sufficient to produce a peroxyacid, a hydroperoxide, a bis(hydroperoxide) and an epoxide. In some embodiments the citramalic acid salt may be a lithium, sodium, potassium, rubidium, cesium, zinc, magnesium, or calcium salt, or a mixture thereof. In other embodiments, the process further comprises contacting citramalic acid or salt thereof and the oxidizing agent with acetic acid, maleic acid or anhydride, citraconic acid or anhydride, or a mixture thereof.

In another aspect, the present invention provides a method of making a wound healing composition comprising contacting an acetoacetate ester or a salt thereof with an oxidizing agent while stirring under conditions sufficient to produce one or more of a peroxyacid, a hydroperoxide, a bis(hydroperoxide), or an epoxide. In some embodiments, the conditions are sufficient to produce a peroxyacid, a hydroperoxide, a bis(hydroperoxide), and an epoxide. In some embodiments, the acetoacetate ester may be methyl acetoacetate or ethylacetoacetate, or a mixture thereof. In other embodiments, the acetoacetate ester salt may be a lithium, sodium, potassium, rubidium, cesium, zinc, magnesium, or calcium salt, or a mixture thereof. In some embodiments, the process further comprises adding citramalic acid.

While a variety of oxidizing agents may be used in such methods, typical oxidizing agents may comprise hydrogen peroxide, barium peroxide, sodium carbonate peroxide, potassium superoxide, or a mixture thereof. In some embodiments, the oxidizing agent is hydrogen peroxide.

In another aspect, the present invention provides a method of making a wound healing composition comprising combining one or more of a peroxyacid, a hydroperoxide, a bis (hydroperoxide), or an epoxide in an aqueous solution. In some embodiments, the method comprises combining a peroxyacid and bis(hydroperoxide) in an aqueous solution. In some embodiments, the peroxyacid is peracetic acid. In other embodiments, the bis(hydro-peroxide) is 3,3-bis(hydroperoxy) butanoic acid or 3-bis(hydroperoxy) butaneperoxoic acid.

In some embodiments, the method further comprises adding a hydroperoxide to the aqueous solution. In some embodiments, the hydroperoxide is one of methylhydroperoxide and hydroxymethyl hydroperoxide. In other embodiments, the method further comprises adding an epoxide to the aqueous solution. In some embodiments, the epoxide is 5-hydroperoxy-5-methyl-1,2-dioxolan-3-one. In some embodiments, the method further comprises adding hydrogen peroxide to the aqueous solution.

In other embodiments, the peroxyacid is peroxycitraconic acid. The peroxy-citraconic acid may be either (2Z)-4-hydroperoxy-3-methyl-4-oxobut-2-enoic acid, (2Z)-4-hydroperoxy-2-methyl-4-oxobut-2-enoic acid, or a mixture thereof. In other embodiments, the peroxyacid is diperoxycitraconic acid, i.e., (2Z)-2-methylbut-2-enediperoxoic acid. In other embodiments, the peroxyacid is peroxycitramalic acid. The peroxycitramalic acid may be either 4-hydroperoxy-2-hydroxy-2-methyl-4-oxobutanoic acid, 4-hydroperoxy-3-hydroxy-3-methyl-4-oxobutanoic acid, or a mixture thereof.

In another aspect, the present invention provides methods of making antimicrobial, chemical oxidizer, and disinfecting solutions comprising any of the above-described methods.

In another aspect, present invention provides methods for treating a wound infection in a subject comprising contacting the infected wound in the subject with a therapeutically effective amount of an above-described composition. Methods of the invention can be used to treat surgical wound, battle wound, accidental wound, thermal burn wound, chemical burn wound, chronic wound, decubitus ulcer, foot ulcer, venous ulcer, laser treatment wound, sunburn, and/or an abrasion.

Generally, the composition is applied to the infected wound at least once, often at least twice a day initially.

In other embodiments, the composition is formulated as a gel, a liquid, lotion, skin patch, irrigation gel, a liquid, lotion, skin patch, a spray, application granules, or a combination thereof.

In yet another aspect, the present invention provides methods for reducing the number of microbes on a surface. Such methods typically include contacting the surface with an antimicrobial product comprising an above-described composition. Yet other aspects of the invention provide a method for reducing the number of infectious vegetative bacteria on a substrate comprising contacting the substrate with an antimicrobial solution comprising an effective amount of an above-described composition. Other aspects of the invention provide a method for reducing the number of bacterial spores on a substrate comprising contacting the substrate with an antimicrobial solution comprising an effective amount of an above-described composition.

In some embodiments, the microbe comprises vegetative bacteria. Within these embodiments, in some instances the microbe comprises bacterial spores, mycobacteria, gram-negative bacteria, vegetative gram-positive bacteria, or a combination thereof.

Yet other aspects of the invention provide methods for preventing and/or reducing bacteria-related diseases in a mammal that result from the mammal's contact with a bacteria-infected substrate. Such methods can include contacting the substrate with an above-described composition.

The details of one or more embodiments of the invention are set forth in the description below. Other features, objectives, and advantages of the invention will be apparent from the description and from the claims.

BRIEF DESCRIPTION OF THE FIGURES

The accompanying drawings, which are incorporated herein and constitute part of this specification, illustrate the presently preferred embodiments of the invention, and, together with the general description above and the detailed description given below, serve to explain the features of the invention. In the drawings:

Figure 2:
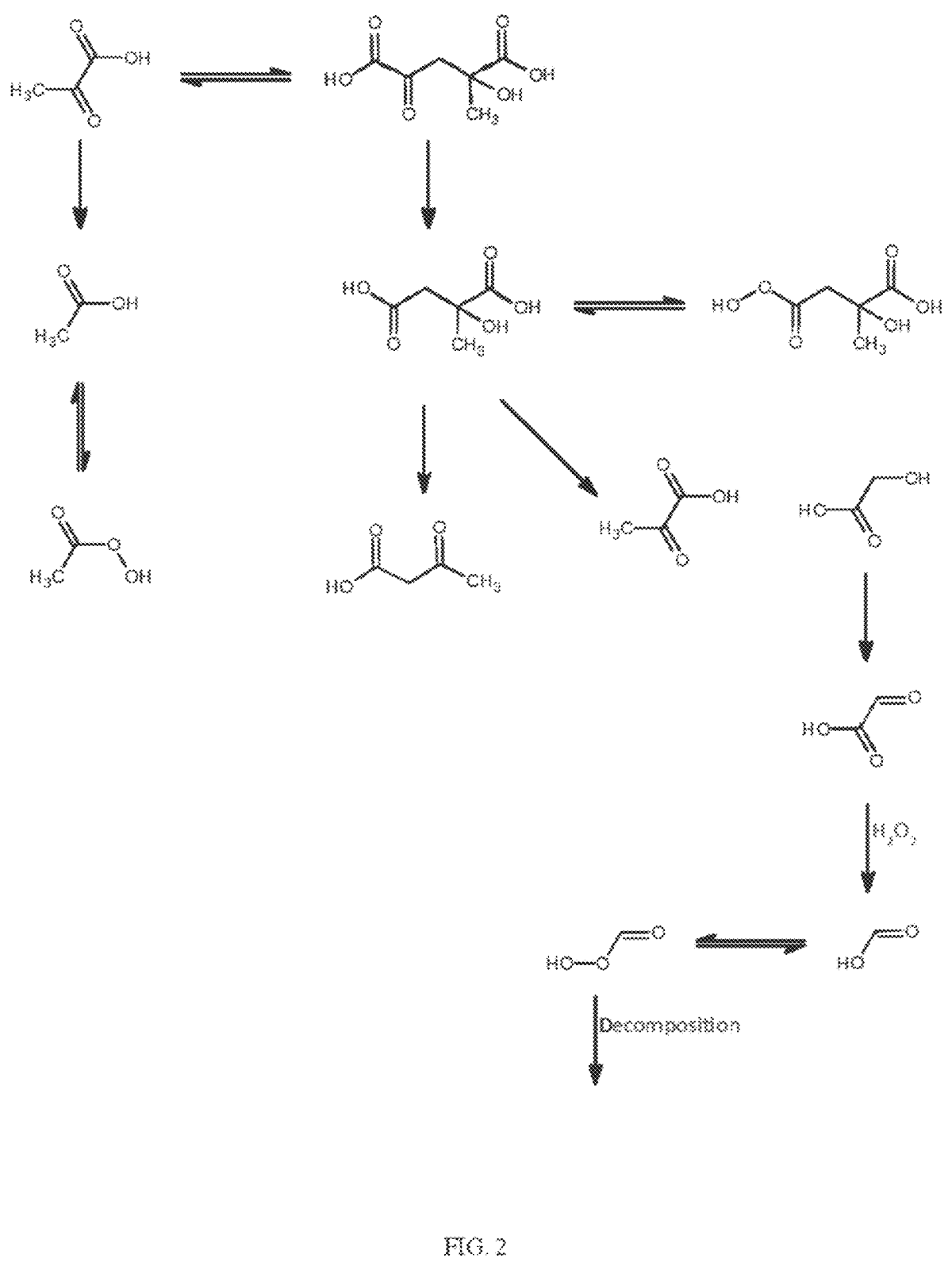

FIG. 2 is a reaction scheme for a reaction comprising pyruvic acid and hydrogen peroxide according to an embodiment of the present invention.

Figure 3:
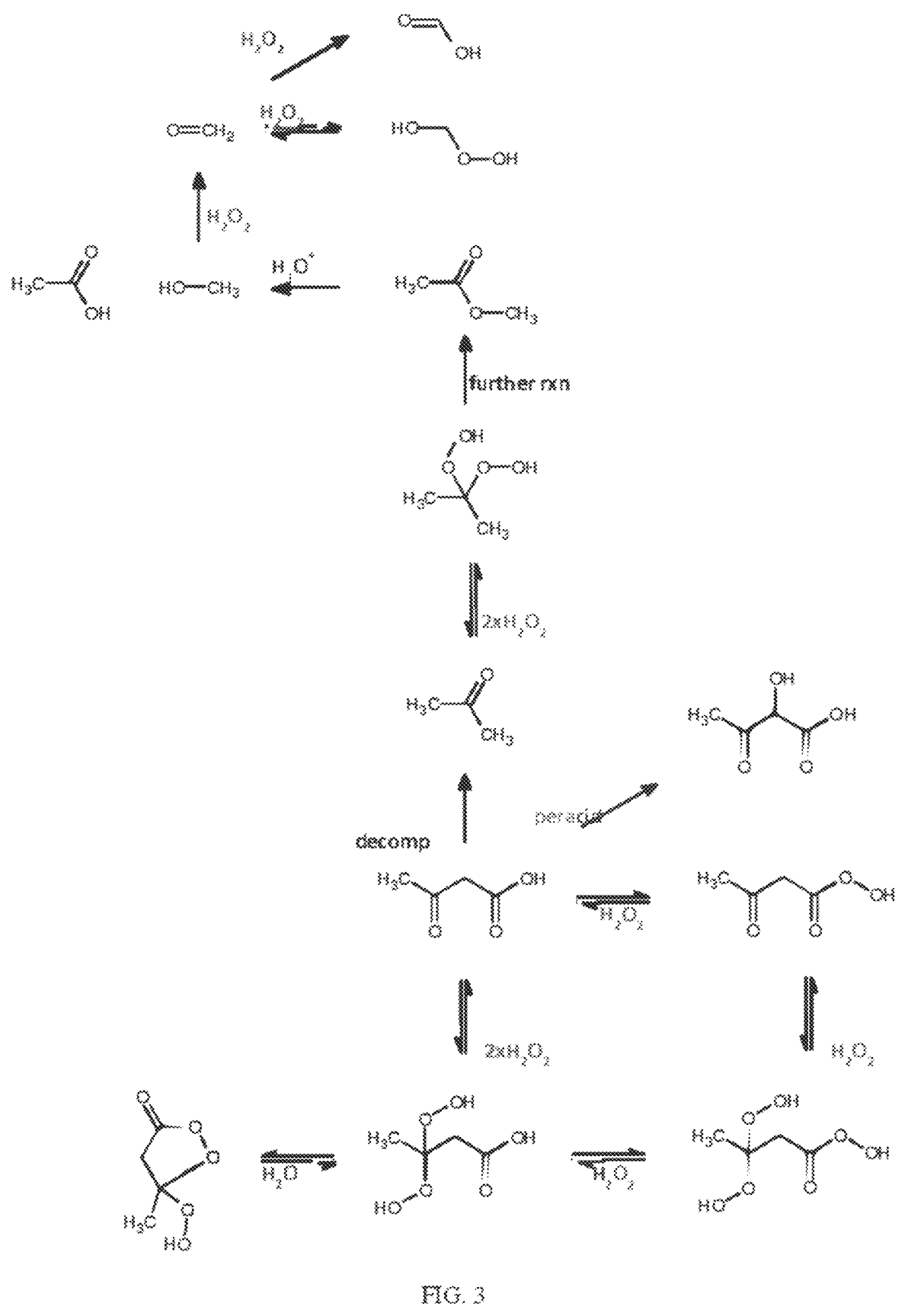

FIG. 3 is a reaction scheme for a reaction comprising acetoacetic acid and hydrogen peroxide according to an embodiment of the present invention.

Figure 4:
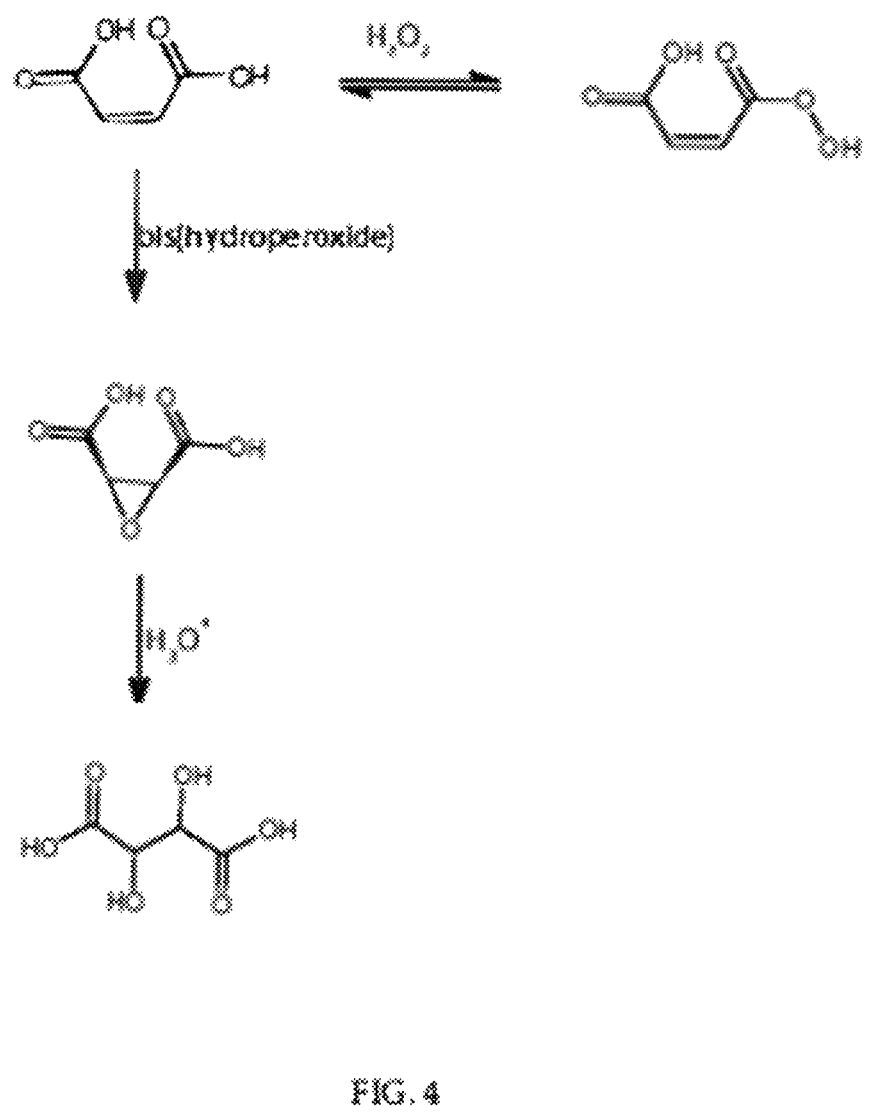

FIG. 4 is a reaction scheme for a reaction comprising maleic acid and hydrogen peroxide according to an embodiment of the present invention.

Figure 5:
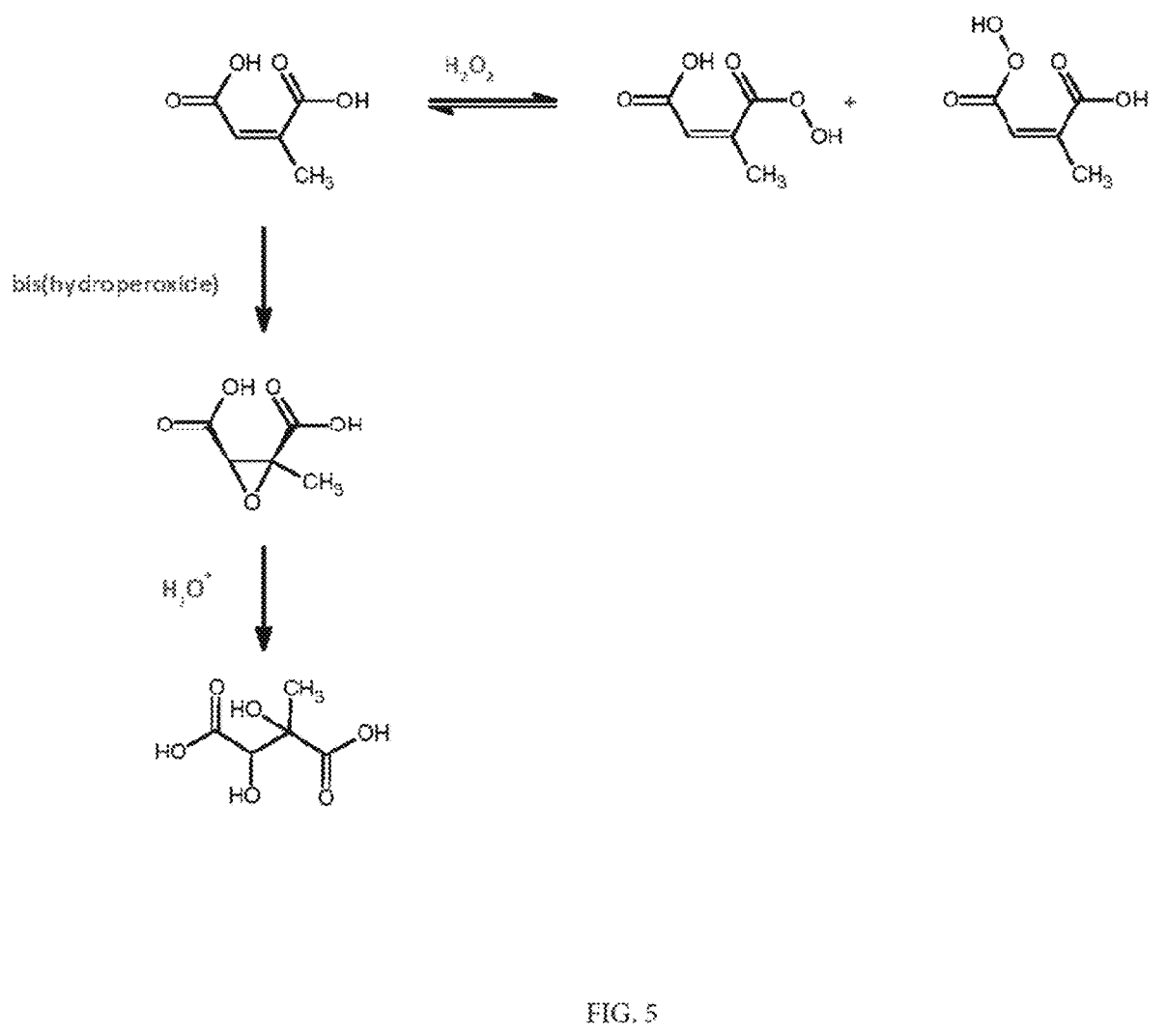

FIG. 5 is a reaction scheme for a reaction comprising citraconic acid and hydrogen peroxide according to an embodiment of the present invention.

DETAILED DESCRIPTION OF THE INVENTION

Figure 1:
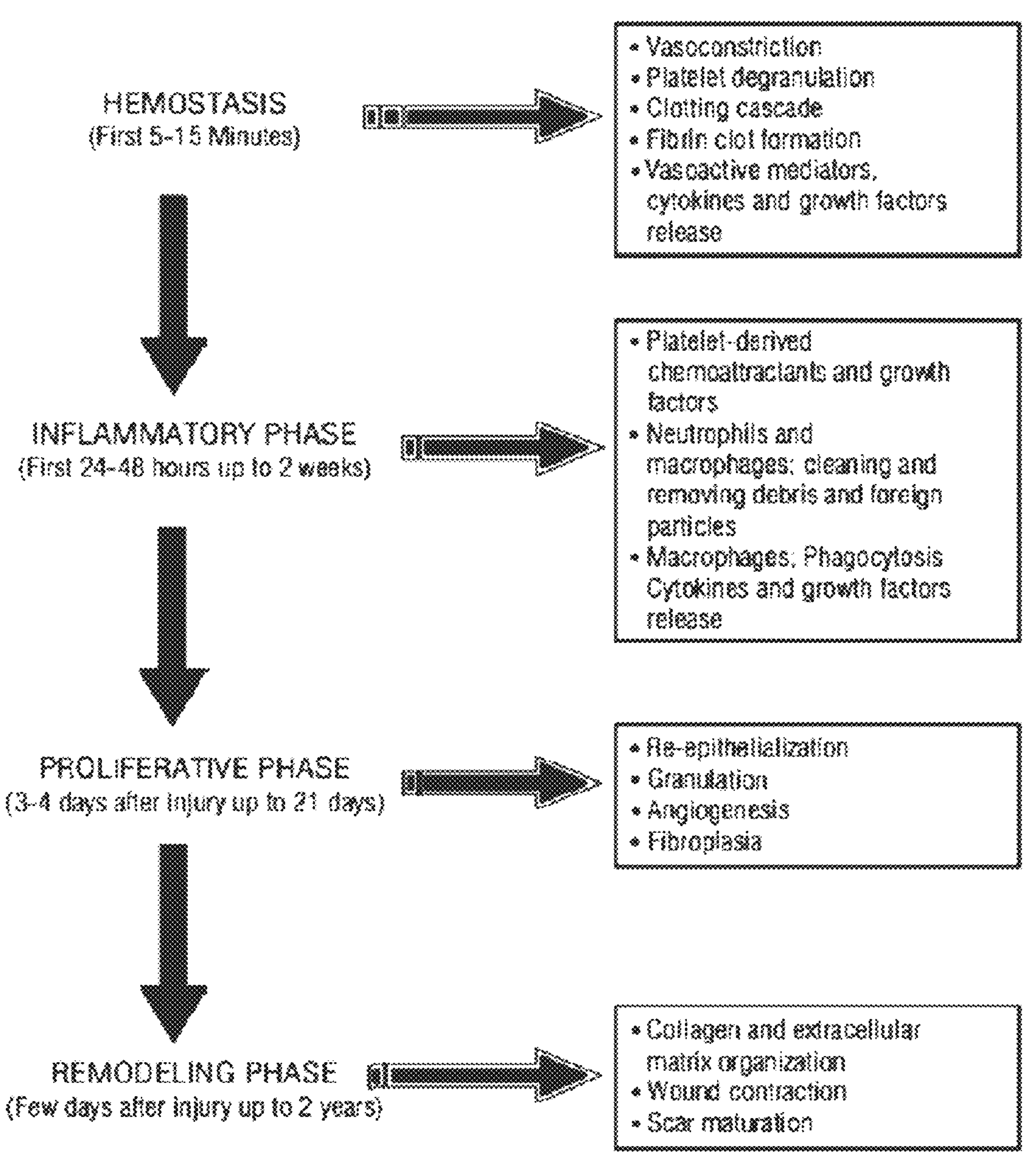
FIG. 1 is a graphic illustration of phases of wound healing.

While various aspects and features of certain embodiments have been summarized above, the following detailed description illustrates a few embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. In other instances, certain structures and devices are shown in block diagram form. Several embodiments are described herein, and while various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers expressing quantities of ingredients, dimensions, reaction conditions, and so forth, used in the specification and claims, are to be understood as being modified in all instances by the term "about".

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

In some aspects, the present invention relates to antimicrobial, disinfecting, and/or wound healing compositions and methods for producing and using the same. The compositions may comprise one or more of a keto acid, a peracid, a hydroperoxide, a bis(hydroperoxide), or an epoxide.

Some aspects of the present invention provide methods for treating a wound on a subject comprising contacting the wound with a therapeutically effective amount of a composition comprising a peracid and a bis(hydroperoxide). In some aspects, the present invention also relates to compositions comprising a peracid and a bis(hydroperoxide), as well as methods for making and using such compositions and mixtures thereof. In some embodiments, the composition further comprises a hydroperoxide, an epoxide, or both.

In general, peracids are compounds of oxidized form of a base organic acid (generally a carboxylic acid) that exist in equilibrium with an oxidizer (generally hydrogen peroxide) and water. One species of peracid with superior regeneration properties are peroxy alpha-keto acid (PKCA) compounds (see U.S. Patent Application Publication No. 2010/0261792). PKCA compounds would generally be composed of an α-keto carboxylic acid, the anion of that α-keto acid, a buffer, and hydrogen peroxide, and the oxidized form of the carboxylic acid. Peroxy pyruvate acid (PPA), for example, may be in equilibrium with pyruvic acid, acetic acid and peracetic acid and other peracids. Peracids may be oxidized from other carboxylic acids, e.g. citric acid, succinic acid, short chain fatty acids, etc.

As used herein, "peracid," "peroxyacid," "percarboxylic," and "peroxy-carboxylic acid," and are used interchangeably herein and refer to a compounds generally have the formula $R(CO_3H)_n$, where, for example, R is an alkyl, arylalkyl, cycloalkyl, aromatic, or heterocyclic group, and n is one, two, or three, and named by prefixing the parent acid with "peroxy-." The R group can be saturated or unsaturated as well as substitut-ed or unsubstituted. Peroxycarboxylic acids can be made by the direct action of an oxidizing agent on a carboxylic acid, by autoxidation of aldehydes, or from acid chlorides, and hydrides, or carboxylic anhydrides with hydrogen or sodium peroxide.

Peroxycarboxylic acids useful in the compositions and methods of the present invention include peroxyformic, peroxyacetic, peroxypropionic, peroxybutanoic, peroxypentanoic, peroxyhexanoic, peroxyheptanoic, peroxyoctanoic, peroxynonanoic, peroxy-decanoic, peroxyundecanoic, peroxydodecanoic, or the peroxyacids of their branched chain isomers, peroxylactic, peroxymaleic, peroxyascorbic, peroxyhydroxyacetic, peroxyoxalic, peroxymalonic, peroxysuccinic, peroxyglutaric, peroxyadipic, peroxypimelic and peroxy-suberic acid and mixtures thereof. In some embodiments, the compositions of the invention utilize a combination of several different peroxycarboxylic acids. For example, in some embodiments, the composition includes one or more C1 to C4 peroxycarboxylic acids and one or more C5 to C11 peroxycarboxylic acids. Especially preferred is an embodiment in which the peroxycarboxylic acid is peracetic acid (C2), peroxy propionic acid (C3), peroxybutanoic acid (C4), peroxysuccinic and peroxymalonic acid. It should be noted that both the peroxy-succinic and peroxymalonic acid may come from the alpha-keto dicarboxylic acids. Furthermore, because these acids exist in the Krebs cycle they are metabolically active.

In some embodiments, the compositions and methods of the present invention include peroxyacetic acid. Peroxyacetic (or peracetic) acid is a peroxycarboxylic acid having the formula: $CH_3COOH$. Generally, peroxyacetic acid is a liquid having an acrid odor at higher concentrations and is freely soluble in water, alcohol, ether, and sulfuric acid.

For clarity, terms used herein are to be understood as described herein or as such term would be understood by one of ordinary skill in the art of the invention. Additional explanation of certain terms used herein, are provided below:

"wt %" refers to the weight percent relative to the total weight of the solution or dispersion.

"Microorganism" is meant to include any organism comprised of the phylogenetic domains of bacteria and archaea, as well as unicellular (e.g., yeasts) and filamentous (e.g., molds) fungi, unicellular and filamentous algae, unicellular and multicellular parasites, viruses, virinos, and viroids.

"Film-forming agent" or "water soluble or water dispersible coating agent," which may be used interchangeably herein, refer to agents that form a film and are employed to provide protective coating to the surface of interest. These agents are either water soluble or water dispersible. These agents are described in further detail below.

"Antimicrobial agent" as used herein refers to a compound or substance having antimicrobial properties "Biocide," as used herein, refers to a chemical agent, typically broad spectrum, which inactivates or destroys microorganisms. A chemical agent that exhibits the ability to inactivate or destroy microorganisms is described as having "biocidal" activity.

"Biofilm" refers to a structured community of microorganisms encapsulated within a self-developed polymeric matrix and adherent to a living or inert surface. "Drying" refers to a process by which the inert solvent or any other liquid present in the formulation is removed by evaporation.

"Disinfectant" as used herein is a chemical that kills 99.9% of the specific test microorganisms in 10 minutes under the conditions of the test. (Germicidal and Detergent Sanitizing Action of Disinfectants, Official Methods of Analysis of the Association of Official Analytical Chemists, paragraph 960.09 and applicable sections, 15th Edition, 1990 (EPA Guideline 91-2)).

"Sterilization" or "sterilant" as used herein refers to the inactivation of all bio-contamination.

"Locus" as used herein, comprises part or all of a target surface suitable to be coated.

Some methods of the invention include contacting a keto acid and oxidizing agent while stirring and under conditions sufficient to produce one or more of a peroxyacid, a hydroperoxide, a bis(hydroperoxide), or an epoxide. In some embodiments, the conditions are sufficient to produce a peroxyacid, a hydroperoxide, a bis(hydroperoxide), and an epoxide. As used herein, unless the context requires otherwise, the term "stir" or "stirring" refers to agitating or act of causing a mixing of the reagents by using an external force such as by using a mechanical stirrer, a magnetic stirrer, a shaker, or any other mechanical, electrical, magnetic, or manual force including simply mixing the reagents manually.

It should be noted that the yield of the reaction is affected by a variety of reaction conditions and reagents used. One of the factors influencing the yield is the reaction temperature. Generally, the rate of reaction increases as the temperature increases, however, a higher reaction temperature can also increase the yield of side-product(s) and/or decomposition to the non alpha-keto peroxyacid. Therefore, the reaction temperature is typically kept at about 0° C. or below, often at about 10° C. or below, and more often at about −20° C. or below. In some embodiments, the reaction temperature is between −10° C. to 10° C.

The concentration of the reagents can also affect the rate and the yield of the reaction. The initial concentration of the oxidizing agent is generally about 12 M or less, typically about 7 M or less, and often about 1 M or less.

The reaction time can also affect the yield. Typically the reaction time ranges from about 4 hours to about 12 hours, often from about 6 hours to about 8 hours, and more often from about 10 hours to about 12 hours.

Methods of the invention are applicable to a wide variety of keto acids, and in particular alpha-keto carboxylic acids. In fact, generally any alpha-keto carboxylic acid can be used as long as any reactive functional group within the alpha-keto carboxylic acid is properly protected. Suitable protection groups for various chemical reactions are well known to one skilled in the art. See, for example, Protective Groups in Organic Synthesis, 3rd ed., T. W. Greene and P. G. M. Wuts, John Wiley & Sons, New York, 1999; Smith and March, Advanced Organic Chemistry, 5th ed., John Wiley & Sons, New York, N.Y., 2001; and Harrison and Harrison et al., Compendium of Synthetic Organic Methods, Vols. 1-8 (John Wiley and Sons, 1971-1996), which are incorporated herein by reference in their entirety. Exemplary alpha-keto carboxylic acids include, but are not limited to, pyruvic acid, alpha-keto butyric acid, alpha-keto valeric acid, alpha-keto glutaric acid, 2-oxo cylopental acetic acid, etc.

Exemplary oxidizing agents that are useful in methods of the invention include, but are not limited to, hydrogen peroxide, barium peroxide, sodium carbonate peroxide, calcium peroxide, sodium perborate, lithium peroxide, magnesium peroxide strontium peroxide, zinc peroxide, potassium superoxide, and the like.

In some embodiments, the methods may comprise additional reagents such as acetic acid or anhydride, maleic acid or anhydride, citraconic acid or anhydride, or a mixture thereof.

In an exemplary embodiment, the method comprises contacting a mixture of pyruvic acid, maleic acid, and citraconic acid with hydrogen peroxide while stirring at a reaction conditions sufficient to produce the reaction products shown in the reaction schemes of FIGS. 2-5.

When describing a chemical reaction, the terms "treating," "contacting," and "reacting" are used interchangeably herein, and refer to adding two or more reagents under appropriate conditions to produce the indicated and/or the desired product. It should be appreciated that the reaction which produces the indicated and/or the desired product may not necessarily result directly from the combination of reagents which were initially added, i.e., there may be one or more intermediates which are produced in the mixture which ultimately leads to the formation of the indicated and/or the desired product.

The reaction is generally conducted in an aqueous solution. Other solvents, such as an organic solvent can also be used in addition to or in place of the aqueous solution. Because it is inexpensive and commercially available in an aqueous solution, typically hydrogen peroxide is used as an oxidizing agent.

The molar ratio of oxidizing agent to keto acid typically ranges from about 0.5:1 to about 2:1, often about 2:1 to about 6:1. A molar ratio above 1:1 is preferred.

In another embodiment, instead of reacting a keto acid or a salt or anhydride thereof with an oxidizing agent under the conditions described herein to produce the disclosed mixture of compounds, the present invention also provides compositions that are admixtures of the key composition components, Compositions according to this embodiment contain hydrogen peroxide, a peracid, such as peracetic acid, and one or more optional com-pounds selected from tartaric acid, formic acid, cis-epoxysuccinic acid, methyltartaric acid, acetic acid, cis-epoxymethylsuccinic acid, maleic acid, citramalic acid and citraconic acid. Compositions according to this embodiment of the present invention may also optionally include oxidized acetoacetate compounds.

While various reaction parameters are disclosed herein, it should be appreciated that the scope of the invention is not limited to these particular reaction parameters.

Various embodiments of the disclosure could also include permutations of the various elements recited in the claims as if each dependent claim was a multiple dependent claim incorporating the limitations of each of the preceding dependent claims as well as the independent claims. Such permutations are expressly within the scope of this disclosure.

Some aspects of the invention disclose a process for forming a stable aqueous composition containing one or more of a peroxyacid, a hydroperoxide, a bis(hydroperoxide), or an epoxide. In some embodiments, the invention discloses a process for forming a stable aqueous composition comprising a peroxyacid and bis(hydroperoxide). In some embodiments the invention discloses a process for forming a stable aqueous composition comprising a peroxyacid, a hydroperoxide, a bis(hydroperoxide), and an epoxide.

Environmental concerns about the effects of certain chemicals on the upper atmosphere have led to some unease about the widespread use of certain disinfectants. Hydrogen peroxide, peracetic acid, persulfates and peroxyhydrates, such as sodium perborate are well known as disinfectant compounds but are highly corrosive and sometimes hard to handle and/or store.

It is therefore particularly desirable that an antimicrobial containing one or more of a peroxyacid, a hydroperoxide, a bis(hydroperoxide), or an epoxide be available for use as a single, stable gel or a viscous solution (sol), although a solid would be satisfactory if it were biodegradable, easily soluble in water, and did not contain significant inorganic dis-solved solids such as are provided by sodium persulfate or sodium perborate. It is also desirable for the antimicrobial to have less odor, be non-corrosive and promote wound healing.

The embodiments disclosed herein overcome the problems of the prior art by providing an aqueous composition comprising stable sols, gels and solids one or more of a peroxyacid, a hydroperoxide, a bis(hydroperoxide), or an epoxide. In some embodiments, the aqueous composition comprises stable sols, gels and solids comprising a peroxy acid and a bis (hydroperoxide). In some embodiments, the peroxyacid is a C2 to C6 peroxycarboxylic acids. In other embodiments, the compositions of the invention provide a combination of several different peroxycarboxylic acids. For example, in some embodiments, the composition includes one or more C1 to C4 peroxycarboxylic acids and one or more C5 to C11 peroxycarboxylic acids. Especially preferred is an embodiment in which the peroxycarboxylic acid is peracetic acid (C2) peroxy propionic acid (C3) peroxybutanoic acid (C4), peroxysuccinic and peroxymalonic acid. Such compositions form carriers for delivering peroxycarboxylic acids for applications related to high level disinfectants/sterilants of vegetative bacteria, spores and biofilms.

The compositions are particularly useful for killing vegetative bacteria and spores at the level acceptable to be called disinfectants. Unlike most peroxy carboxylic compounds, it was discovered that the non alpha-keto peroxyacid compounds in combination with keto peroxyacids do not require an acid catalyst for efficient synthesis and are effective against biofilms. Without the need for a toxic catalyst for synthesis, the mixture of the embodiments disclosed herein typically contains water, hydrogen peroxide, a peroxyacid, a hydroperoxide, a bis(hydroperoxide), and an epoxide, all of which work synergistically and are beneficial to healing of a wound.

Many of the parent compounds (i.e., the corresponding carboxylic acids) of the embodiments disclosed herein are present within nearly all living cells and play significant roles in essential cellular metabolism. For example, the parent carboxylic acid compounds of peroxypyruvic acid, peroxy oxaloacetate, peroxy alpha-keto glutarate, are key compounds within the TCA cycle, the predominant energy producer for cellular metabolism. The parent compound of peroxy alpha keto butyric acid, i.e. alpha keto butyric acid, is involved in the metabolic production of succinyl-CoA which is also used in the TCA cycle and thus contributes to cellular energy production. Alpha keto valeric acid, the parent compound of peroxy alpha keto valeric acid, is an intermediate in protein synthesis and the biosynthesis of the amino acids such as leucine and valine. Alpha keto valeric acid is involved in gluco-neogenesis in cells. Pyruvate is involved in producing energy for hypoxic cells during wound healing through glycolysis. The potential harmful effects of the ROS can be mediated by alpha-keto acids. In addition, pyruvate is involved in protecting DNA during hypoxia and is an indirect metabolic contributor to collagen deposition and angiogenesis in wound healing. Moreover, pyruvic acid accelerates the debridement of dead skin in both wounds and burns.

In some embodiments, the compositions comprise acetoacetic acid. Acetoacetic acid is one of the ketone bodies (along with 3-hydroxybutyric acid and acetone, although acetone is just a byproduct), which are major energy sources for the body, particularly during starvation. Ketone bodies are involved in pathways related to the Kreb's cycle, lipogenesis, sterol biosynthesis, glucose metabolism, β-oxidation of fatty acids, mitochondrial electron transport chain, intracellular signal transduction pathways, hormonal signaling, and the microbiome (Cotter, D. G., et al., *Am. J. Physiol, Heart Circ. Physiol.,* 2013, 304, H1060-H1076). It has been tied to skin formation/biosynthesis in rats (Edmond, J., *J. Biol. Chem.,* 1974, 249, 72-80). Additionally, it was just recently found to upregulate osteoblasts and in-crease bone formation (Saito, A., et al. *Biochem. Biophys. Res. Comm.,* 2016, 473, 537-544).

Because acetoacetic acid can be converted into acetyl-CoA in vivo, its ability to affect biological processes is extremely high. However, its presence in the solution is unexpected because acetoacetic acid is an unstable compound that reacts intramolecularly and irreversibly, producing acetone and carbon dioxide. Thus, it is expected to be unstable in all solvents and even as a solid compound.

However, acetoacetic acid represents a rather unique case where a compound is stabilized by the addition of hydrogen peroxide, whereas normally the addition of a per-oxide leads to chemical oxidation/degradation. This stabilization is caused by the formation of a range of possible peroxide "adducts" with its ketone functionality and possibly its carboxylic acid. Because both moieties are required for intramolecular "self-destruction", the formation of these other forms slows down the decomposition of the compound. Peroxide adducts may include 3,3-bis(hydroperoxy) butanoic acid, 3,3-bis(hydroperoxy) butaneperoxoic acid, 3-oxobutane-peroxoic acid, and 5-hydroperoxy-5-methyl-1,2-dioxolan-3-one. This stabilization is shown in the reaction scheme of FIG. 3. The compositions may be further stabilized by citramalic acid or an acetoacetate ester, such as methyl or ethyl acetoacetate.

In some embodiments, the compositions may comprise peroxycitraconic acid. The peroxycitraconic acid may be either (2Z)-4-hydroperoxy-3-methyl-4-oxobut-2-enoic acid, (2Z)-4-hydroperoxy-2-methyl-4-oxobut-2-enoic acid, or a mixture thereof. In other embodiments, the compositions may comprise diperoxycitraconic acid, i.e., (2Z)-2-methylbut-2-enediperoxoic acid. In other embodiments, the antimicrobial composition further comprises peroxycitramalic acid. The peroxycitramalic acid may be either 4-hydroperoxy-2-hydroxy-2-methyl-4-oxobutanoic acid, 4-hydroperoxy-3-hydroxy-3-methyl-4-oxobutanoic acid, or a mixture thereof.

Additionally, it was particularly unexpected that stable compositions of peracids and bis(hydroperoxides) could be prepared, since peracids are very strong oxidizing agents even at a pH of 2 to 8 because the water soluble peracids are decomposing to form free radicals.

For the purpose of this invention a "stable" composition is one which maintains sufficient physical properties and active oxygen content long enough to be useful, about twelve months. One important factor that is that "stable" does not imply static. That is, compositions of the present invention may be constantly undergoing a series of internal reactions. This is true of all liquid solutions to a degree, particularly for aqueous ones. However, this is especially true for compositions of the present invention, which have a large number of reversible and effectively irreversible reactions occurring at all times.

Studies show that many widely used wound antiseptics have undesired cytotoxicity, and while some do kill bacteria at a sufficient level, they often do not promote a relatively fast wound healing. In many cases, irrigation of open fracture wounds with an antibiotic solution offers no significant advantages over the use of a nonsterile soap solution and may in fact increase wound-healing problems.

To be useful, topical antiseptics should be toxic to bacteria but should have no significant toxicity to underlying tissues, and ideally, they should also preserve or enhance host defense against infection. The present invention provides a method for treating wounds including, but not limited to, surgical, traumatic, chronic and burn wounds. Methods of the invention promote wound healing and typically rapidly kill high levels of viruses, vegetative bacteria, fungi, mycobacteria and spores. Unlike many conventional antiseptics available today, compositions and methods of the invention eliminate bacteria, enhance body's defense system, and enhance the healing process. Without being bound by any theory, it is believed that these benefits are achieved at least in part by the synergistic effect of the parent alpha-keto acids working together with resultant alpha-keto peracid and a non-alpha keto peroxyacid. It is believed that the synergetic effect results in energy generation and serves as intermediates in the generation of other biomolecules that are useful in wound healing.

In addition, the combination of the peracids and bis(hydroperoxides) disclosed in the present embodiments can kill high levels of bacteria and spores in biofilms and in high protein environments without being corrosive and having virtually no cellular toxicity issues.

In some embodiments of the invention, the compositions may be useful for at least one of dental cleaning, wound decontamination after exposure to chemical biological warfare agents, or wound healing decontamination after exposure to chemical biological warfare agents. Use of the composition for the latter two uses is particularly important as the skin is a primary route of exposure to chemical agents that may be used as weapons of mass destruction. In these embodiments, the composition may include at least one peroxyacetic acid at an equilibrium concentration of from 0.1 ppm to 10 weight percent, based on the weight of the composition. In one embodiment, the peroxyacid may be present at a concentration of less than 5 weight percent. In this embodiment, the peroxyacid may be a ready-to-use solution or a dilatable solution, which enables easy distribution of the composition.

It should be appreciated that because the stability of peracids and bis(hydro-peroxides) are often limited, in many instances compositions of the invention can include the presence of the parent carboxylic acid. As used herein, the term "parent carboxylic acid" refers to the corresponding carboxylic acid in which the peracid is derived from or is degraded into under a typical storage or production conditions. In some embodiments, the parent carboxylic acid is present in the composition of the invention in an amount of about 120.4 mM or less, typically, about 12.4 mM or less, more typically, about 6.2 mM or less, often about 2.5 mM or less, more often, about 1.2 mM or less, still more often about 0.62 mM or less, yet more often about 0.31 mM or less, and most often about 0.062 mM or less.

Still in other embodiments, compositions of the invention can include hydrogen peroxide. Typically, the amount of hydrogen peroxide present in the wound healing compositions of the invention is about 715 mM or less, typically about 71.5 mM or less, more typically about 35.8 mM or less, often about 14.3 mM or less, more often about 7.2 mM or less, still more often about 3.6 mM or less, yet more often about 1.8 mM or less, and most often about 0.35 mM or less.

Furthermore, coatings of composition according to the present invention have a tendency to lose their antimicrobial activity over time, which is believed to be the result of evaporation of the neat peracid. One aspect of the present invention adds a magnesium salt to the composition to form a salt of the peracid, which testing has shown to retain antimicrobial activity over a lengthy accelerated aging test. Accordingly, compositions according to the present invention optionally further include a magnesium salt. The magnesium salt can be a salt of the keto acid, or a magnesium salt such as magnesium, hydroxide, magnesium carbonate, magnesium acetate tetrahydrate, and the like.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, inter-changeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims. All references cited herein are incorporated in their entirety by reference.

EXAMPLES

The present invention is described more fully by way of the following non-limiting examples. Modifications of the examples will be apparent to those skilled in the art.

Example 1

Five milliliters of 30% hydrogen peroxide at 0-1° C. was stirred using a magnetic stir bar. 84-μL aliquots of pyruvic acid were added approximately every 90 s for 19 aliquots (totaling 27 min). During addition of the pyruvic acid and in the time spent stirring afterwards, temperature of the ice bath was measured in the 0-6° C. range. After the final pyruvic acid addition, the product sat in the bath slowly warming to room temperature. 98 min after the last pyruvic acid addition, stirring was terminated.

The reaction products were measured by HPLC analysis several times during the first 40 days after the reaction. The first measurement was performed just 2.4 hr after the final pyruvic acid addition.

Another sample was collected when the reaction was only 5 days old. After 5 days, the majority of the two dimer species have reacted. That citramalic acid is their primary product is evident by the large increase in its peak. Peracetic acid is also a major component at this point. Significant amounts of the oxidized acetoacetic acid species and the main product of their hydrolysis, 2,2-bis(hydroperoxy) propane, are also present.

Another sample was collected after 40-days. The presence/absence of each individual component directly detectable by HPLC is shown in Table 1:

TABLE 1

| Compound | This Work (at 40 Days) |
| --- | --- |
| Hydrogen Peroxide ($H_2O_2$) | ✓ |
| Nitrate | ✓ |
| Hydroxymethyl Hydroperoxide (HMHP) | ✓ |
| Tartaric Acid | × |
| Formic Acid | ✓ |
| Performic Acid | ✓ |
| cis-Epoxysuccinic Acid | |
| Hydroperoxyacetic acid (HPAA) | ✓ |
| Methyl Hydroperoxide (MHP) | ✓ |
| Methyltartaric Acid | ✓ |
| Peracetic Acid | ✓ |
| Acetic Acid | ✓ |
| Permaleic Acid | ✓ |
| cis-Epoxymethylsuccinic Acid | ✓ |
| Oxidized Acetoacetic Acid-1 (O-AAA-1) | ✓ |
| 2,2-Bis(hydroperoxy)propane (2,2-HBPP) | ✓ |
| Unknown 1 (~7.65 min) | ✓ |
| Maleic Acid | ✓ |
| Citramalic Acid | ✓ |
| Oxidized Acetoacetic Acid-2 (O-AAA-2) | ✓ |
| Fumaric Acid | |
| Oxidized Acetoacetic Acid-3 (O-AAA-3) | ✓ |
| Citraconic Acid | ✓ |
| Unknown 2 (~16.3 min) | × |
| Mesaconic Acid | ✓ |

Example 2

Compositions capable of forming shelf-stable coatings containing the magnesium salt of peroxyacetic acid were prepared by drying solutions containing a magnesium salt, acetic acid, hydrogen peroxide, peracetic acid, and poly (ethylene glycol) (PEG). The starting magnesium salt was magnesium hydroxide, magnesium carbonate, or magnesium acetate tetrahydrate (an anhydrous magnesium acetate salt would also be effective since it is being dissolved in a water-containing mixture). The acetic acid/hydrogen peroxide/peracid source was an aqueous solution (called "PAA Source" in this document) usually containing 8-12 wt % peracid (peracetic acid), 15-22 wt % hydrogen peroxide, and 14-20 wt % acetic acid. Coatings were also be made in the presence of silica particles (up to 2.8%). Finally, the remainder of the solution typically consisted of water, but the short-chain alcohols methanol, ethanol, and isopropanol were also successfully used, with the shortest chains being the most successful.

A typical coating-solution mixture consisted of the following, which was used immediately after mixing:

4.1 wt % magnesium acetate tetrahydrate
20 wt % PAA Source
20 wt % PEG 3350
55.9 wt % water Magnesium acetate tetrahydrate concentrations in the 1.8-6.5 wt % range were used successfully, with the best peracid recoveries occurring at higher concentrations. PAA Source concentrations of 8-72 wt % were found to yield stable peracid salts. PEG concentrations of 0-30 wt % were tested successfully. PEG 3350 and PEG 8000 both yielded coatings containing stable peracid salts.

In some embodiments, the coating-solution mixture (i.e. decontaminating composition) will use a PAA source having 8% peracetic acid, 15 wt % hydrogen peroxide and 14 wt % acetic acid, diluted 8 wt % to 72 wt %. This translates to peracetic acid concentrations from 0.64 wt % to 5.76 wt %; hydrogen peroxide concentrations from 1.2 wt % to 10.8 wt %; and acetic acid concentrations from 1.12 wt % to 10.08 wt %.

In some embodiments, the coating-solution mixture (i.e. decontaminating composition) will use a PAA source having 12% peracetic acid, 22 wt % hydrogen peroxide, and 20 wt % acetic acid, diluted 8 wt % to 72 wt %. This translates to peracetic acid concentrations from 0.96 wt % to 8.64 wt %; hydrogen peroxide concentrations from 1.76 wt % to 15.84 wt %; and acetic acid concentrations from 1.6 wt % to 14.4 wt %.

In some embodiments, the coating-solution mixture (i.e. decontaminating composition) will use a PAA source having 8-12% peracetic acid, 15-22 wt % hydrogen peroxide, and 14-20 wt % acetic acid diluted 8 wt % to 72 wt %. This translates to peracetic acid concentrations from 0.64 wt % to 8.64 wt % (6400 ppm to 86400 ppm); hydrogen peroxide concentrations from 1.2 wt % to 15.84 wt % (12000 ppm to 158400 ppm); and acetic acid concentrations from about 1.12 wt % to 14.4 wt % (11200 ppm to 144000 ppm).

The composition of the present invention have utility in numerous household products. The present invention thus also provides an antimicrobial product containing the compositions of the present invention. In some embodiments, the product is a household care product. Within such embodiments, in some cases the house hold care product is selected from hard surface cleaners, deodorizers, fabric care compositions, fabric cleaning compositions, manual dish detergents, automatic dish detergents, floor waxes, kitchen cleaners, bathroom cleaners, and combinations thereof. In other embodiments, the antimicrobial product is selected from hard surface cleaners, deodorizers, fabric care compositions, fabric cleaning compositions, manual dish detergents, automatic dish detergents, floor waxes, kitchen cleaners, bathroom cleaners, and combinations thereof. Antimicrobial products of the invention can be used in a wide variety of settings including, but not limited to, in health care facilities such as hospitals, rehabilitation, assisted living facilities, etc.

In other embodiments, the antimicrobial product is a medical device disinfectant. Still in other embodiments, the antimicrobial product is used as a disinfectant for aseptic filling equipment. Yet in other embodiments, the antimicrobial product is used in an aseptic food processing system. In other embodiments, the antimicrobial product is used as a disinfectant for biofilms in water systems. Still in other embodiments, the antimicrobial product is used as a disinfectant for waste water treatment.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights that include alternative embodiments to the extent permitted, including alternate, interchange-able and/or equivalent structures, functions, ranges or steps to those claimed, whether or not such alternate, interchangeable and/or equivalent structures, functions, ranges or steps are disclosed herein, and without intending to publicly dedicate any patentable subject matter.

Example 3

This example compared the effectiveness of the composition of the invention as a decontamination (DC) product after skin exposure to the chemical warfare agent VX, as compared to that of Reactive Skin Decontamination Lotion (RSDL), which is a mixture of potassium 2,3-butanedione monoximate (KBDO) and diacetylmonoxime (DAM) in a solvent of polyethylene glycol monomethyl ether (MPEG) and water.

Experimental Methods:

Animals: Male guinea pigs [Hartley, Crl (HA) BR] ranging in weight from 340-503 gm at the time of experimentation were obtained from Charles River (Canada). After arrival, the animals were maintained in quarantine for at least 5 days prior to use in an Association for Assessment and Accreditation of Laboratory Animal Care International (AAALACI) accredited animal care and use facility. On the morning of an experiment, around 0800 hr, animals were weighed, the fur was carefully removed from the left side with electric clippers, and excess loose fur was removed with a vacuum. An exposure site was outlined with an indelible marker at approximately the same location on the left side of each animal midway between the spine and the ventral midline. The animals remained unanesthetized during the entire experiment. After exposure to the VX and decontamination with the composition or RSDL, animals were housed in individual cages without bedding in a fume hood for the duration of the experiment (24 hr). Food and water were provided ad libitum after exposure and DC.

Materials: Each exposure day a 50 pl aliquot of neat VX was obtained from the Chemical Exclusion Area, United States Army Medical Research Institute of Chemical Defense (USAMRICD; Maryland, USA). RSDL was purchased in sealed packages from First Line Technology, (Chantilly, VA). The composition according to the invention, containing peracids, was prepared. A 1:6 dilution in deionized water was prepared according to the manufacturer's formula each test day.

VX Exposure: Neat VX was applied in a fume hood to the marked exposure site of each animal, using either a 5 pl Hamilton syringe for volumes greater than 1 pl, or a 0.5 pl or 1.0 pl Hamilton digital syringe for volumes less than 1 pl. Animals were hand restrained by a trained technician for exposure.

Decomtamination procedure: Two minutes after applying VX to the skin, the exposure site was decontaminated with RSDL or the composition. Animals were hand restrained by a trained technician during the DC procedure. RSDL was applied with an applicator made by stapling ¼ (25 mm×50 mm) of a RSDL sponge pad to a wooden tongue depressor. Applicators for the composition were made by stapling a similar size folded gauze pad to wooden tongue depressors. A fresh applicator of each DC product was used on each animal. The RSDL applicators were made just before the start of the experiment and were placed into small plastic bags until use. The composition applicators were wetted with 10 ml of the diluted composition solution just before DC. Ten ml was sufficient to saturate the applicator pad without run-off based on previous experience using dilute bleach or soap and water. RSDL and the composition DC were performed by swiping the applicator across the exposure site 10 times from a head to tail direction. Neither DC product was removed after application.

Experimental Design: VX dose-lethality curves were generated for RSDL and the composition, based on 24 hr responses. After exposure and DC, each animal was monitored continuously until the onset of toxic signs, and then at 2 and 4 hr after DC, and again 24 hr after exposure. A modified stage-wise adaptive dose design was used to generate the VX dose-lethality curves for each DC product. The first stage utilized the classic up-down dose design of Dixon to estimate the LD50 of VX for each DC product. Briefly, one animal at a time was challenged with a dose of VX for each DC product during Stage1. After the 24 hr response was determined, the next animal in each DC product group received a higher (if alive at 24 hr) or lower (if dead at 24 hr) dose of VX, depending on the response of the previous animal. The up-down procedure continued until four response reversals were observed. The 24 hr responses for each DC product from Stage 1 were analyzed by probit analysis using SAS NLIN and special purpose probit programs developed by Battelle (Columbus, Ohio) to generate an interim $LD_{50}$ estimate. The next stages of the experiment used 3-8 animals per stage and various doses of VX in each stage for each DC product to improve the $LD_{50}$ estimate and generate 95% confidence intervals (CI) by both the Fieller's and the delta methods. The VX doses in each stage were selected to improve the $LD_{50}$ estimate and 95% CI based from all stages. Interim probit analyses were run after each stage, and the experiment was stopped when the ratio of the upper delta 95% CI minus the lower delta 95% CI divided by 2 times the $LD_{50}$ estimate was <0.4. A total of 15 and 26 animals were used to generate the RSDL and composition dose-lethality curves, respectively.

Statistical Analysis: A final probit analysis was conducted on all stages from the 24 hr responses for RSDL and the composition. The slopes, $LD_{50s}$ as well as the $LD_1$, $LD_{10}$, $LD_{16}$, $LD_{30}$, $LD_{70}$, $LD_{84}$, $LD_{90}$, and $LD_{99}$ with their respective 95% CI were calculated by both Fieller's and delta methods. Probit estimates were calculated using both target and actual doses of VX and were not statistically different; therefore, the target doses were used for all statistical comparisons and in the graphs and tables. LD50 estimates for RSDL and the composition were compared using SAS and another specialized probit program, which determined whether the ratio of the $LD_{50s}$ was statistically different at $p<0.05$. A significant ($p<0.05$) difference was achieved when the delta 95% CI of the $LD_{50}$ ratio did not include the value of 1. The slopes of the dose-lethality curves were compared according to Zar. A protective ratio (PR) defined as $LD_{50}$ of VX in animals treated with the DC product divided by the $LD_{50}$ of VX in untreated animals was estimated, using a historic value of 140 μg/kg in fur-clipped unanesthetized guinea pigs (Clarkson, personal communication) for the denominator in the ratio. The PR expresses the magnitude of the increase in the $LD_{50}$ by the DC product. Another ratio called an absolute efficacy ratio (AER) was also calculated. The AER was defined as the $LD_{10}$ of VX in animals treated with a DC product divided by the dermal $LD_{90}$ of VX in untreated animals. A $LD_{90}$ value of 188 μg/kg generated in hair-clipped, unanesthetized guinea pigs (Clarkson, personal communication) was used for the denominator for the AER.

TABLE 2

Twenty-four hour VX $_{LD50}$ Estimates in Guinea Pigs Decontaminated with the Composition or RSDL 2 Min After Dermal Exposure

| DC Product | Number of Animals | Slope of the Dose-Lethality Curve | 24 hr VX $LD_{50}$, μg/kg, p.c. (95% Cl) | Estimated Protective Ratio[1] |
|---|---|---|---|---|
| Composition | 26 | 6.4 | 5959 (4858-7309) | 42.6 |
| RSDL | 15 | 12.7 | 3380 (2921-3910) | 24.1 |
| Efficacy Ratio 50% Survival | | Composition/RSDL = 1.8 p<0.05 | | |

Estimated using a 24-hour dermal VX $LD_{50}$ of 140 μg/kg in fur-clipped unanesthetized guinea pigs (Clarkson, personal communication)

Table 3 summarizes the results based on $LD_{10}$s. The 24 hr dermal $LD_{10}$ of VX was 3755 μg/kg in animals decontaminated with the composition and 2681 μg/kg in animals decontaminated with RSDL. The composition was 1.4-fold more effective than RSDL; this difference was not significant. Also, presented in Table 3 is the ratio of the VX $LD_{10}$ in animals receiving DC to the VX $LD_{90}$ in animals that were not treated with a DC product. The $LD_{10}/LD_{90}$ ratio for the composition was 20 and the ratio for RSDL was 14.

TABLE 3

Twenty-Four Hour VX $LD_{10}$ Estimates in Guinea Pigs Decontaminated with the Composition or RSDL 2 Min After Dermal Exposure

| DC Product | Number of Animals | 24 hr VX $LD_{10}$, μg/kg, p.c. (95% Cl) | $LD_{10}/LD_{90}$ 1 |
|---|---|---|---|
| Composition | 26 | 3755 (2390-5500) | 20 |
| RSDL | 15 | 2681 (2096-3429) | 14 |
| Efficacy Ratio 90% Survival | | Composition/RSDL =1.4 | |

VX $LD_{90}$ of 188 μg/kg was used for the denominator. This value was estimated from the dose-lethality curve generated in fur-clipped, unanesthetized guinea pigs (Clarkson, personal communication)

The AER expresses the magnitude of the increase in the $LD_{10}$ relative to the untreated $LD_{90}$, and is a more operationally relevant measure of efficacy than the PR, especially if the slopes of the dose-lethality curves are significantly different. Military requirements documents prescribe 80-90% survival for acceptance of new medical countermeasures against nerve agent intoxication.

Figure 6:
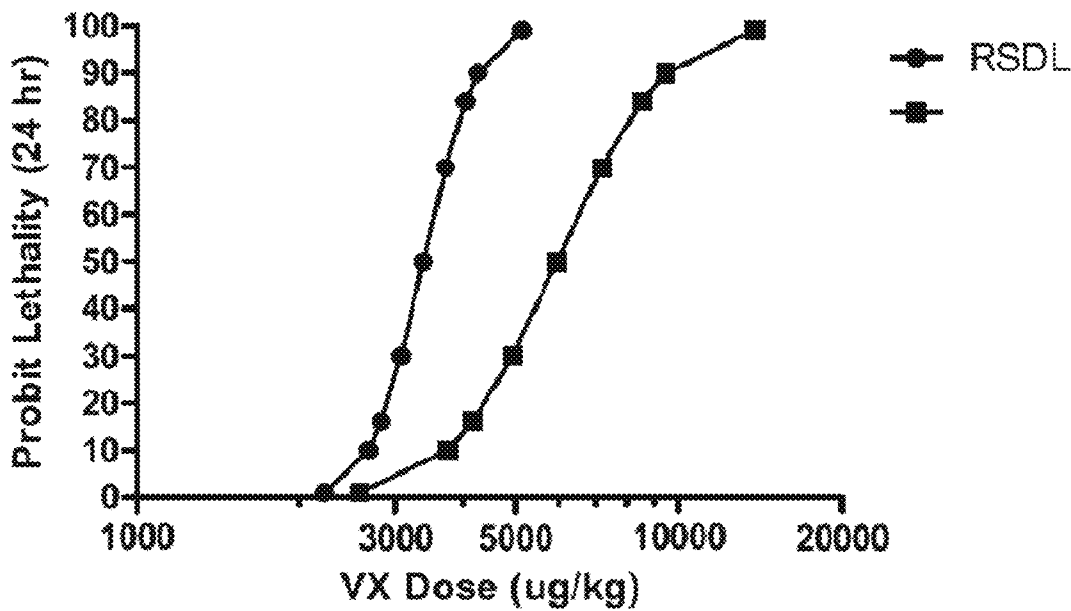
FIG. 6 is a graph of the VX dose lethality curves in animals decontaminated with either RSDL or a composition according to the invention after cutaneous exposure.

Results:

FIG. 6 graphs the probit dose-lethality curves for VX in composition and RSDL-decontaminated animals, and Table 2 summarizes the results based on $LD_{50}$s. A total of 15 and 26 animals were needed to generate the dose-lethality curves for RSDL and the composition, respectively, using the stopping criteria described in the methodology. The 24 hr dermal $LD_{50}$ of VX was 5959 μg/kg in animals decontaminated with the composition and 3380 μg/kg in animals decontaminated with RSDL. The composition was 1.8-fold ($p<0.05$) more effective than RSDL. The slope of the composition dose-lethality curve was significantly ($p<0.05$) different from the slope of the RSDL dose-lethality curve. The estimated PR (treated to untreated) was 42.6 for the composition® and 24.1 for RSDL.

A comparison of the $LD_{50}$ estimates showed that the composition was significantly more effective than RSDL. In addition, the slope of the composition dose-lethality curve was more shallow than the slope of the RSDL curve. It is not unusual for the slope of the dose-lethality curve to become more shallow as the effectiveness of medical countermeasures against organophosphate intoxication increases. However, Braue et al. 1 observed no difference in the slopes of the dose-lethality curves for RSDL, 1% soapy water, and 0.5% bleach, even though RSDL was greater than 3-fold more effective than the other two DC products; all three slopes were similar to the slope for the composition in the study.

When the slopes are different, comparison of $LD_{50}$s may not be as valuable, because the lower doses of agent in the curve with the shallower slope may still show lethality. Since the slope of the composition dose-lethality curve was shallower than the slope of the RSDL curve, the ratio of the LD10 doses of VX were compared. This might reveal whether the shallower slope of the composition dose-lethality curve resulted in higher lethality at lower doses of VX compared to RSDL. The $LD_{10}$ was selected because military requirements documents prescribe 80-90% survival rates as criteria for accepting new medical countermeasures for use by warfighters. The composition was still more effective than RSDL, but the ratio of the $LD_{10s}$ was not significantly different. This was probably due to the wider confidence intervals around the $LD_{10}$ than the $LD_{50}$ estimate. The ratio of the $LD_{10}$ in the animals receiving DC to $LD_{90}$ in animals not receiving DC provides another way of comparing efficacy which is independent of the slope. This ratio value represents the number of $LD_{90}$s of exposure that can be tolerated without sustaining more than 10% lethality. This value was 20 for the composition and 14 for RSDL.

Example 4

This example involved an In vitro evaluation of the composition of the invention by nuclear magnetic resonance (NMR) evaluation Summary: A decontamination (DC) solution containing the composition was examined for its ability to breakdown intact chemical warfare agents (CWAs) in vitro using nuclear magnetic resonance spectroscopy (NMR). Agents examined were HD, GD, VX, VR and A-232. For all agents except HD, the assessment was done with one-dimensional heteronuclear spin quantum correlation (HSQC) techniques. This approach has been successfully utilized for similar studies examining the breakdown kinetics in enzyme systems using comparable agent levels. For HD, direct one-dimensional proton experiments were used.

Figure 7:
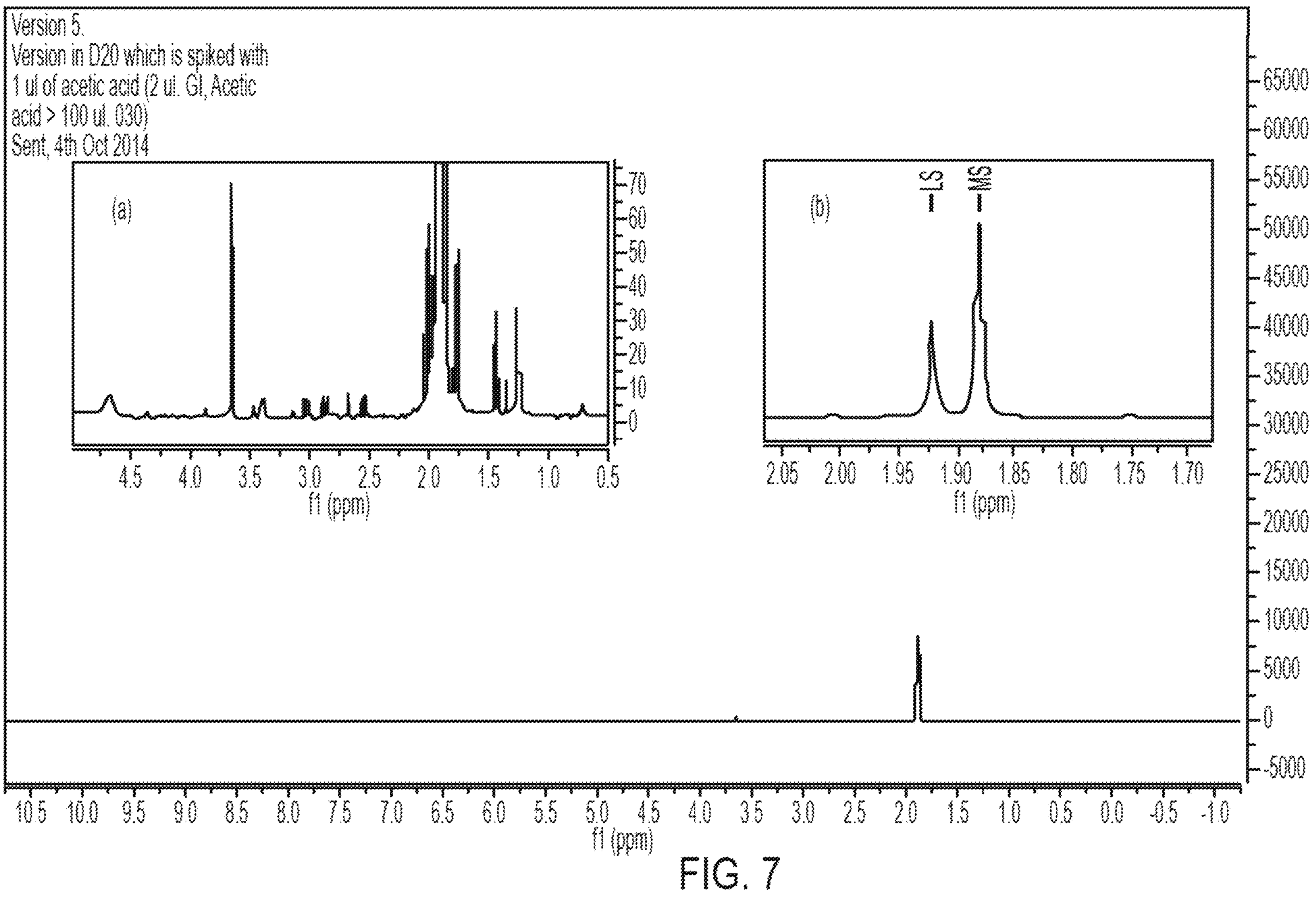
FIG. 7 is a depiction of the proton NMR spectrum of a composition according to the invention.

Composition Sample Preparation: Dilutions of the composition were made with 99.5% D2O from Sigma-Aldrich. Final concentrations of 2%, 4% and 6% were achieved after mixing 100 μL of CWA with 500 μL of the composition. FIG. 7 shows the 1H spectrum of the composition using presat sequence for water suppression; the inset (a) shows 1000X vertical expansion of the region with trace impurities and inset (b) shows the two major peaks of the composition at 1.92 and 1.88 ppm, respectively.

Agent Preparations: CWAs were provided in deuterated solvents by the MRICD Chemical Exclusion Area where the concentrations of each of the CWAs were determined independently. For all experiments, 100 μL of CWA was mixed with 500 μL of the composition. For kinetic determinations, the peak area at time zero was set equal to the final amount of CWA after dilution with the composition. Time zero amounts were 912.8, 175.7, 95.3, 88.0 and 77.7 μg for HD, GD, VX, VR and A-232, respectively.

Instrumentation: NMR data on VX, VR, GD and A-232 were collected on a 3-channel Bruker Avance III Ultrashield 500 MHz NMR spectrometer (Bruker Biospin, Billerica, MA) equipped with a Z-gradient 5 mm BBO probe head at 25° C. Topspin (Bruker 3.2pl6) was used for data acquisition and processing. Dynamics Center v2.2 was used for kinetic analysis, and results were exported to PDF and Excel formats, which later were analyzed using GraphPad's Prism5 for Windows.

NMR data on HD were collected on an Agilent (Agilent Systems, Santa Clara, CA) 4-channel DD2 Actively Shielded 600 MHz NMR instrument equipped with a 5 mm PFG Penta probe at 25° C. VNMRJ 3.2 was used for data collection and processing, and the results were exported to Excel for kinetic analysis.

Figure 8:
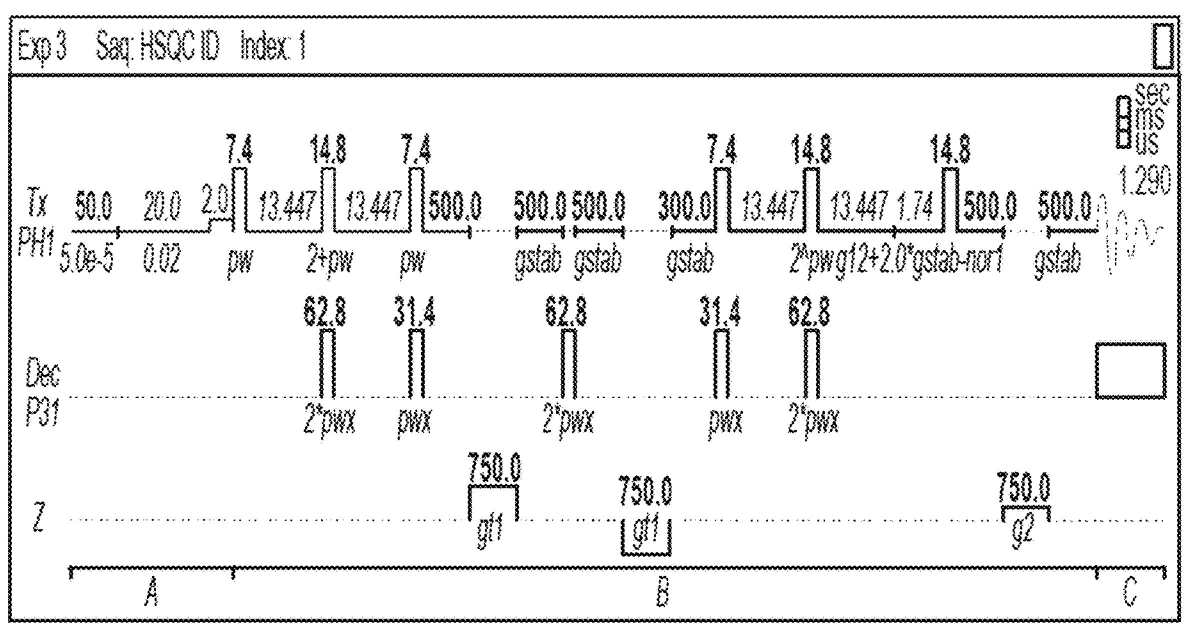
FIG. 8 is a depiction of a pulse sequence of modified gradient 1H—X 1D-HSQC for chemical warfare agents (CWAs).
Figure 9:
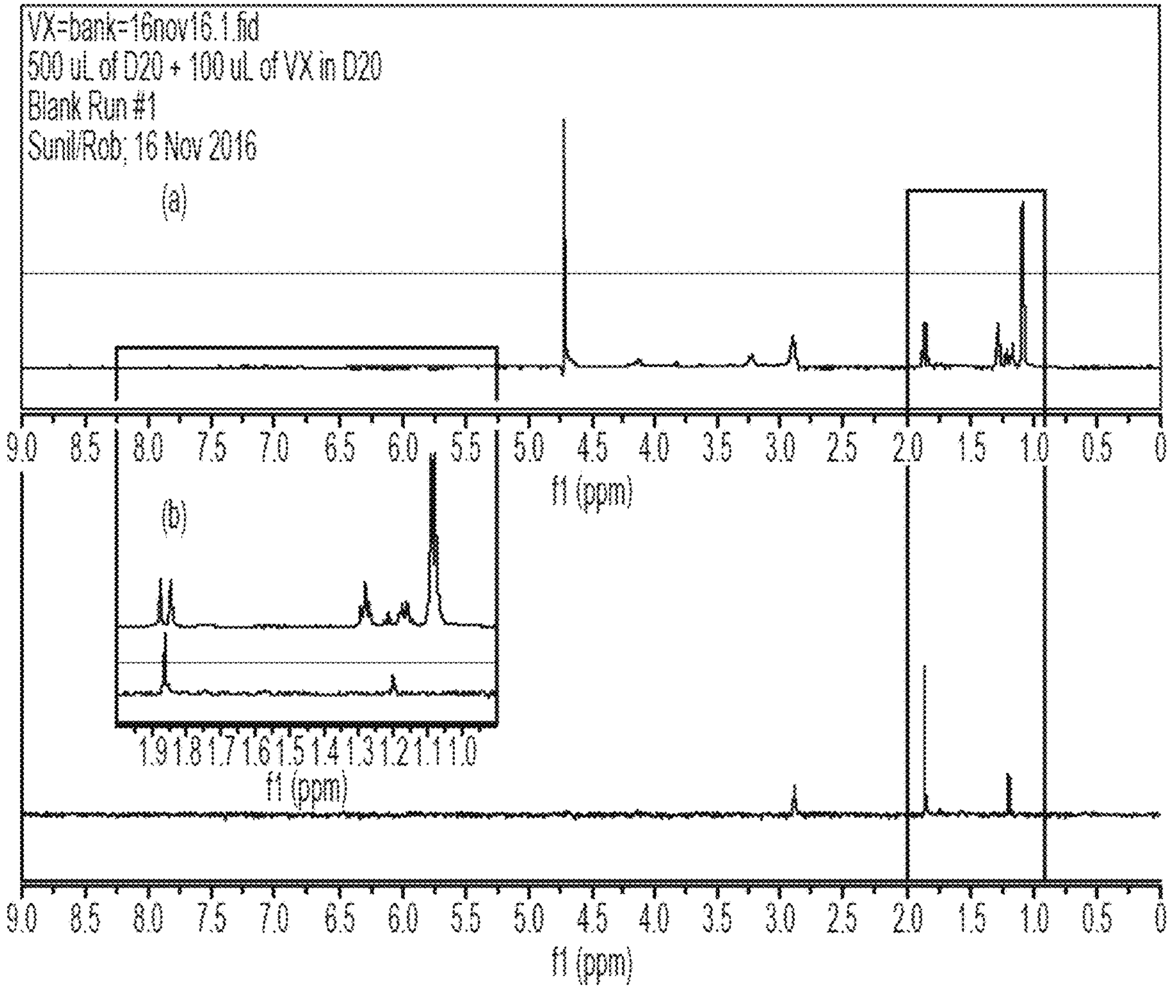
FIG. 9 is a depiction of an NMR spectrum of (a) chemical warfare agent VX and (b) its decontamination product.

Experimental Design: For all experiments 100 μL of CWA was added to 500 μL of the composition or D20 as per experimental protocol. Proton one-dimensional experiments were carried out with or without pre-saturation of water signal. The offset carrier frequency was adjusted on water resonance, and minimum power level was used to saturate the water signal without distortion/perturbation of the neighboring resonances. All samples were temperature equilibrated, and the probe was tuned to the respective frequencies followed by gradient shimming. The time required for gradient shimming (dead time) was noted and taken into account for all kinetic calculations. Ninety degree pulse width, X pwx, and decoupling calibrations were done on both the proton and phosphorus channels and saved in the probe files, respectively. Proton one-dimensional pulse sequence (s2pul) was used in HD, and modified gradient $^1$H—X 1D-HSQC (FIG. 8) was used for all other CWAs. (A representation of the gHSQCID experiment is presented in FIGS. 9*a* and 9*b* showing expansion of the region of interest of methyl resonances —P—$CH_3$ at 1.96 and 1.20 ppm, respectively.) Optimization of the proton signal at 1.96 ppm in $^1$H—X Heteronuclear Single Quantum Coherence (HSQC) was done by observing $^nJ_{HX}$ coupling constant (Table 4) and changing the J parameter in the pulse sequence to the observed value. The ratio of G1/G2 gradient strength was also optimized to give an optimum signal, and this is based on the gyromagnetic ratio of proton and phosphorus.

TABLE 2

Coupling Constants for Various Chemical Warfare Agents

| $^n$JHX | Coupling Constant (Hz) |
|---|---|
| $^2$JHX VX | 17.5 |
| $^2$JHX GD | 18.5 |
| 2J HX VR | 17.5 |

Proton spectra were acquired on all CWAs to check the purity of the compound and to determine whether any degraded products were present. Background spectra were acquired on all composition samples before 100 μL of respective agent was added to the NMR tube. All gHSQCID spectra were acquired with the same parameters (nt/ns=16; relaxation delay (d1)=2 sec; dummy scans (ss/ds)-0; acquisition time (at)=1.7s; number of data points (np)-32K, Fourier number (fn)-64K) and processed using Bruker Biospin and/or VNMRJ with zero filling to 64K data size and applying exponential weighting function line broadening (LB) of 1.0 Hz. Peak integrals were manually defined based on methyl peaks from starting material and methyl peaks from intermediate compound. These methyl peaks were identified by using an edited version of (gradient heteronuclear single quantum coherence with adiabatic pulses) gHSQCAD two-dimensional experiment and the peaks' chemical shifts. Total acquisition time for all kinetic experiments was adjusted to 1 hour. Triplicate data sets were collected for each of the four CWA and blank runs. Blank runs were done in 99.8% D20 without the composition and monitored for a total of 1 hr. Kinetic data are summarized in Tables 5 and 6.

TABLE 5

Half-Lives of CWAs Decontaminated with the composition Solutions

| | T½ (min) (95% Confidence Interval) | | | | |
|---|---|---|---|---|---|
| | Blank | 2% Composition | 4% Composition | 6% Composition | RSDL |
| HD | 8.6 (8.4-8.8) | 51.6 (51.4-51.7) | 27.9 (27.7-28.1) | 19.7 (19.55-19.79) | NA |
| GD | N/A | 1036 (907-1210) | 797 (709-910) | 915 (680-1398) | NA |
| VX | N/A | 39.7 (38.5-41.0) | 19.2 (18.9-19.5) | 13.7 (13.43-13.89) | 4.6 (4.4-4.9) |
| VR | N/A | 30.0 (29.3-30.7) | 14.9 (14.6-15.1) | 12.5 (12.3-12.8) | NA |
| A-232 | N/A | 163 (135-206) | 95.3 (85-108) | 54.3 (50.6-58.6) | NA |

TABLE 6

Percentage of CWA Remaining after 60 Min Decontamination with the Composition Solution

| | Blank | 2% | 4% | 6% |
|---|---|---|---|---|
| HD | 0 | 45 | 24 | 13 |
| GD | 97 | 93 | 90 | 95 |
| VX | 100 | 34 | 11 | 8 |
| VR | 100 | 27 | 7 | 5 |
| A-232 | 100 | 90 | 61 | 48 |

*Decomposition of HD in the blank was due to hydrolysis, while oxidative breakdown was the major route observed in the composition.

breakdown was the major route observed in the composition.

To determine the rate of hydrolysis of the CWAs in the reaction mixture, the gHSQC method was used, and the peak corresponding to the starting material was manually integrated. This integration area was then applied to all spectra to obtain the change in concentration over time. In the case of HD, one-dimensional proton spectra were used. The peak corresponding to the methylene (—CH2—) peak of the starting material was integrated manually and then was applied to all spectra collected.

Figure 10:
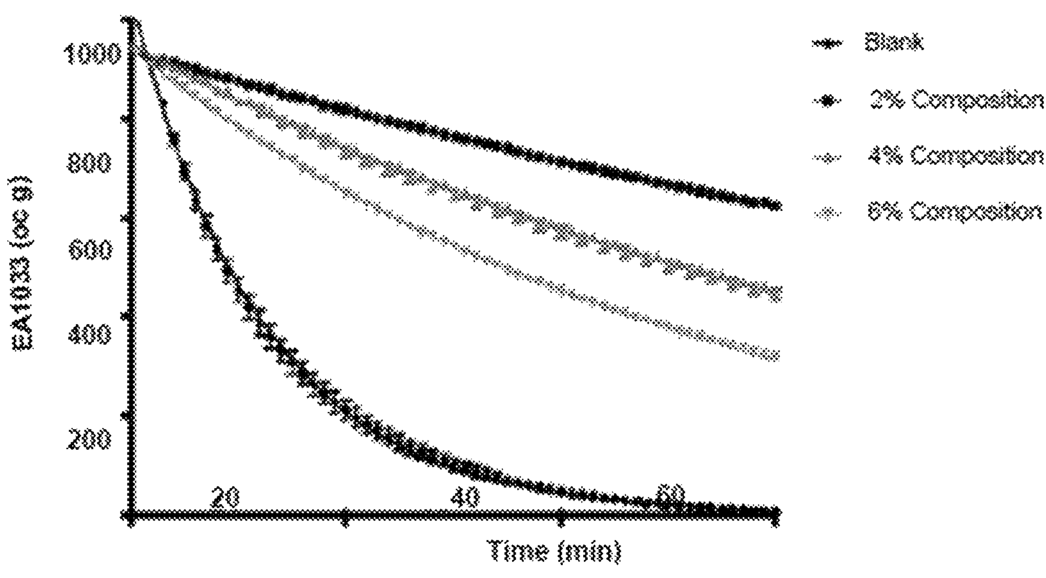
FIG. 10 is a graph showing decontamination (DC) of chemical wafare agent HD by various concentrations of a composition according to the invention fit to a one-phase decay curve.
Figure 11:
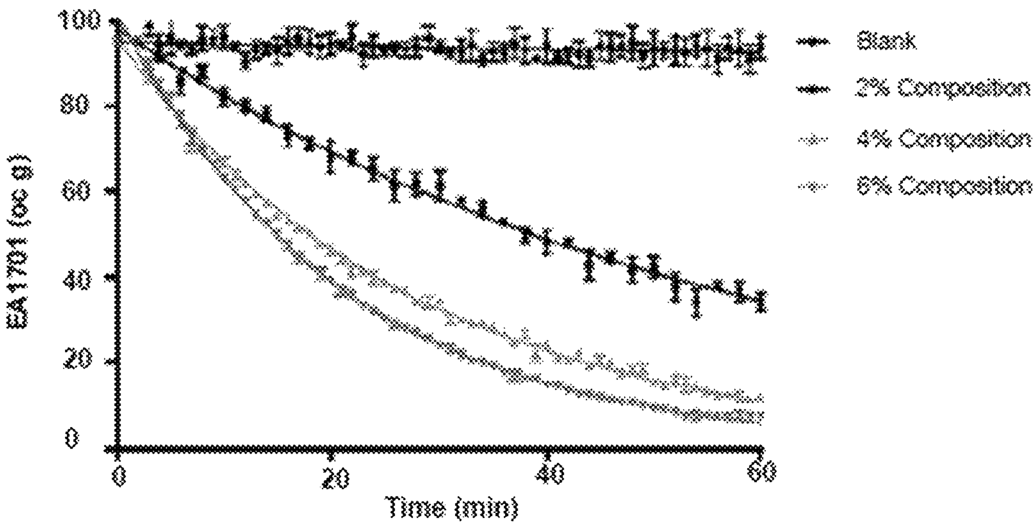
FIG. 11 is a graph showing decontamination of chemical wafare agent VX by various concentrations of a composition according to the invention fit to a one-phase decay curve.

Results: In blank composition solution (water), HD rapidly hydrolyzed with a t1/2 of 8.6 minutes (Table 5 and FIG. 10). In contrast, GD, VX, VR and A-232 were found to be stable, demonstrating that 97-100% of the starting concentration remained at the end of the experiment (Table 6). In the composition, HD breakdown was slower at all concentrations relative to the blank. Half-lives were approximately 52, 28 and 20 minutes for 2, 4 and 6%, respectively (Table 5). The differential breakdown kinetics observed between the blank and the composition solutions can be explained by the products formed. Breakdown products identified in the blank indicate hydrolysis as the primary route, whereas in the composition solutions, oxidative processes were involved. The composition demonstrated no decontamination efficacy for GD (Table 5). The amount remaining at the end of the experiment was 90% or greater at all the composition concentrations (Table 6). A concentration-dependent breakdown was observed for VX (FIG. 11) and VR in the composition. Half-lives were 39, 19 and 13 minutes for 2, 4 and 6%, respectively, for VX and 30, 15 and 12 minutes for 2, 4 and 6%, respectively, for VR (Table 5). Some breakdown of A-232 was observed in the composition compared to blank, but the rates were much less than those observed for either VX or VR in the composition (Table 5). The kinetic data are summarized in Tables 5 and 6.

Conclusion: At the time of writing, measurements by NMR of the rate at which RSDL breaks down CWAs had only been done for RSDL vs VX. It was determined that RSDL breaks down VX with a half-life of 4.6 minutes. Although the composition was slower than RSDL at breaking down VX, it was fast enough to support testing the composition in vivo.

Example 5

This example involved an initial skin DC efficacy evaluation of the composition and its comparison to RSDL following skin application of VX in guinea pigs.

Animals: The same type of animals were secured and prepared as described in Example 3.

Materials: An aliquot of neat VX was obtained from the USAMRICD Chemical Exclusion Area each exposure day. RSDL was purchased in sealed packages from First Line Technology, Chantilly, VA. The composition, containing a concentrated solution of 12.1% peracid and 22.3% hydrogen peroxide, and an aliquot was diluted to a 2% peracid concentration in deionized water each test day.

Agent exposure: A vial of neat VX was obtained from the USAMRICD Chemical Exclusion Area each exposure day and placed in a fume hood at room temperature. VX was applied with a Hamilton 0.5 μl, 1 μl or 5 μl syringe equipped with a blunt tip needle and digital dispenser to the outlined exposure area.

DC Procedures: Decontamination procedures were conducted in the same manner described in Example 3. 3.

Experimental Design: Experimental data were generated as described in Example

Statistical Analysis: A final probit analysis was conducted on all stages from the 24 hr responses for each DC material. The slopes and LD50s as well as the LD1, LD10, LD16, LD30, LD70, LD84, LD90, and LD99 were calculated with their respective Fieller's and Delta 95% confidence intervals (CI). LD50 estimates for RSDL and the composition were compared using another specialized SAS program (Battelle, Columbus, Ohio), which determined whether the ratio of the LD50s was statistically different at $p<0.05$. A significant ($p<0.05$) difference was achieved when the delta 95% CI of the LD50 ratio did not include the value of 1.[5] A protective ratio (PR) defined as the LD50 of VX in animals treated with the DC product divided by the LD50 of VX in untreated animals was estimated, using a historic value of 140 μg/kg[8] in fur-clipped un-anesthetized guinea pigs for the denominator in the ratio.

Figure 12:
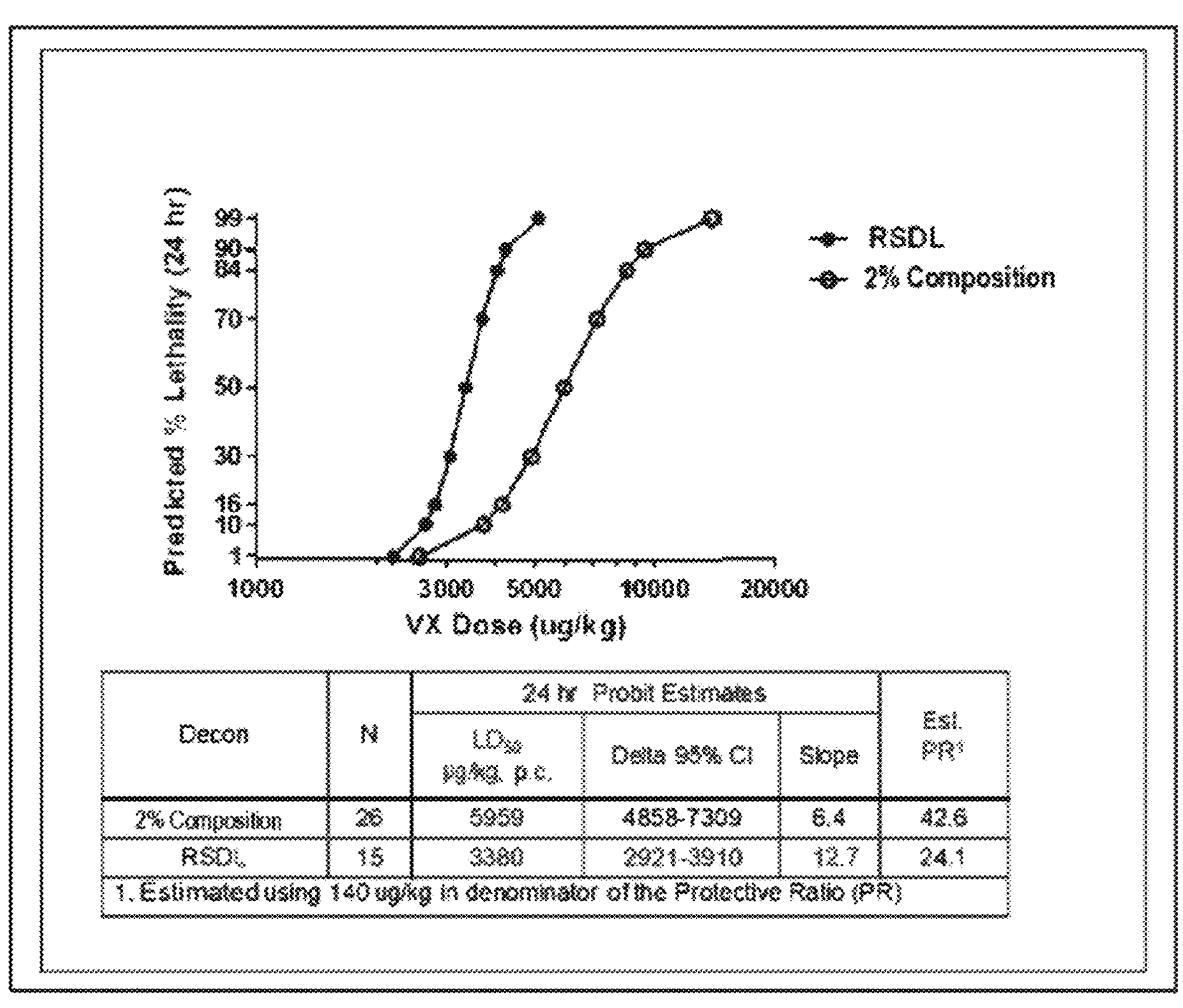
FIG. 12 a depiction of RSDL and a composition according to the invention (2%) skin decontamination (DC) efficacy following topical application of agent VX. Decontamination was performed 2 min after agent application. The graph shows the probit-predicted dose-lethality curves based on 24 hr mortality. The table shows calculated probit estimates, group sizes, and estimated protective ratios (PR).

Results: FIG. 12 graphs the probit predicted dose-lethality curves for VX in the composition- and RSDL-decontaminated animals and tabulates the probit estimates at 24 hr for the $LD_{50}$. 95% CI and slope. A total of 15 and 26 animals were needed to generate the dose lethality curves for RSDL and the composition, respectively, using the stopping criteria described above. The 24 hr dermal $LD_{50}$ of VX was 5959 μg/kg in the composition-decontaminated animals and 3380 μg/kg in RSDL-decontaminated animals. The composition was 1.8-fold ($p<0.05$) more effective than RSDL. The estimated PR (treated/untreated) was 42.6 for the composition and 24.1 for RSDL. Since the gauze used with the composition was more abrasive than the sponge used with RSDL, the possibility that the higher level of protection provided by the composition may have been due to increased physical removal.

Conclusion: The results of this initial assessment of the efficacy of the composition suggest that it is more effective than RSDL as a skin DC product for the nerve agent VX. However, the RSDL PR in this study is considerably lower than PRs reported by either Braue et al.1 or Clarkson et al.8 These investigators reported RSDL PRs of 66 (N=37) and 52 (N=53), respectively, using the same DC timing and procedures. We have no explanation for the difference in their results from ours except for the smaller sample size used in the current experiment and the inherent variability in responses of animals.

Example 6

This example analyzed delayed skin DC efficacy of the composition and RSDL following topical A-232 application in guinea pigs.

Animals: Animal information is the same as in previous studies.

Materials: An aliquot of neat A-232 was obtained from the USAMRICD Chemical Exclusion Area each exposure day. RSDL, purchased in sealed packages from First Line Technology, Chantilly, VA. The containing a concentrated solution of 12.1% peracid and 22.3% hydrogen peroxide as prepared. Aliquots were diluted to a 2% peracid concentration in deionized water according to the manufacturer's formula each test day.

Agent Exposure: Exposure methods for A-232 were the same as those described for VX in previous studies.

DC Procedure: RSDL and composition applicators and DC procedures were the same as described in previous studies. Water was applied with gauze applicators saturated with 10 ml using the same procedures utilized for RSDL and the composition. A fresh applicator of each DC product was used on each animal.

Experimental Design: This study consisted of two experiments, each with 30 animals. Animals in each experiment were randomly allocated into three DC treatment groups of 10; the groups were RSDL, 2% composition, and water. In Experiment 1, animals were exposed topically to $5\times LD_{50}$s of neat A-232, and skin DC was performed at 3 hr after agent application or at the onset of signs, whichever occurred first. In Experiment 2, animals were exposed topically to $10\times LD_{50}$ of neat A-232, and skin DC was performed at 1 hr after agent application or at the onset of signs, whichever occurred first. The clinical condition of each animal was evaluated at 2 hr and 4 hr after DC, early the next morning (0700-0800) and at 24 hr after exposure. Clinical assessment scores (CAS) were given to the animals at each observation time according to the following scale: 0=normal appearance and behavior; 1=mildly intoxicated (characterized by slight lethargy and/or minor signs, but animal is upright and ambulates by itself); 2-moderately intoxicated (noticeable lethargy and signs, but animal is upright and will ambulate if prodded); 3=severely intoxicated (the animal is prone, not ambulatory, with prominent signs but is conscious and can lift head); and 4=very severely intoxicated (animal is prostrate, unresponsive with or without pronounced signs).

Statistical Analysis: None conducted.

Results: Experiment 1: Six of the 30 animals developed signs of nerve agent intoxication prior to the three-hour DC time. All but one of these six animals were decontaminated at the onset of signs with their assigned DC product, and all subsequently died prior to 24 hr. The one animal that was not decontaminated developed signs within 10 min after exposure and was dead by 13 min after exposure. The remaining 23 animals reached the 3 hr DC time without exhibiting any visible signs of nerve agent intoxication. Each was decontaminated, and the survival results are summarized in Table 7. The survival rates for the RSDL, composition (2%), and water DC groups were 9/9 (100%), 7/8 (88%) and 4/6 (67%), respectively. One animal in the composition DC group was removed from the study due to a technical error.

TABLE 7

Summary of Survival from Experiment 1

| DC Product | Survival Rate | | | |
|---|---|---|---|---|
| | 2 hr | 4 hr | Next AM | 24 hr |
| RSDL | 9/9 | 9/9 | 9/9 | 9/9 |
| Composition (2%) | 8/8 | 8/8 | 7/8 | 7/8 |
| Water | 6/6 | 6/6 | 5/6 | 5/6 |

Table 8 shows the clinical assessment scores at 2 and 4 hr after DC, the next morning, and at 24 hr after exposure in the subset of 23 animals that were sign-free when DC was performed 3 hr after dermal exposure. Only one animal exhibited signs at 2 hr; this was an RSDL animal. The remaining animals that developed signs did so between 4 hr after DC and the next morning, at which time one composition animal was found dead, and two of the animals in the water group were severely affected. At 24 hr, 4/9 RSDL-decontaminated animals were normal and the remaining animals were scored as mild to moderately affected; 4/7 surviving composition animals were normal looking, and the remaining animals were mild to moderately affected. In the water DC group at 24 hr, 1/4 surviving animals appeared normal, two animals died, and three were mild to moderately affected.

TABLE 8

Clinical Assessment Scores in Individual Animals at 2 and 4 Hr after DC, the Next Morning and at 24 Hr after Exposure to $5xLD_{50}$ A-232 (Experiment 1)

| DC Product | | Clinical Assessment Scores | | | |
|---|---|---|---|---|---|
| RSDL | Animal # | 2 hr | 4 hr | Next AM | 24 hr |
| | 288 | 0 | N/A | 1 | 2 |
| | 291 | 0 | N/A | 0 | 1 |
| | 294 | 0 | N/A | 0 | 1 |
| | 297 | 0 | 0 | 0 | 0 |
| | 299 | 0 | 0 | 0 | 0 |
| | 301 | 0 | 0 | 0 | 1 |
| | 308 | 0 | 0 | 0 | 0 |
| | 311 | 2 | 2 | 1 | 2 |
| | 313 | 0 | 0 | 0 | 0 |

TABLE 8-continued

Clinical Assessment Scores in Individual Animals at 2 and 4 Hr after DC, the Next Morning and at 24 Hr after Exposure to $5xLD_{50}$ A-232 (Experiment 1)

| DC Product | | Clinical Assessment Scores | | | |
|---|---|---|---|---|---|
| RSDL | Animal # | 2 hr | 4 hr | Next AM | 24 hr |
| Composition (2%) | 287 | 0 | N/A | 0 | 1 |
| | 292 | 0 | N/A | Dead | Dead |
| | 293 | 0 | N/A | 1 | 2 |
| | 296 | 0 | N/A | 0 | 0 |
| | 305 | 0 | 0 | 1 | 1 |
| | 309 | 0 | 0 | 0 | 0 |
| | 314 | 0 | 0 | 0 | 0 |
| | 315 | 0 | 0 | 0 | 0 |
| Water | 289 | 0 | N/A | 1 | 0 |
| | 290 | 0 | N/A | 1 | 2 |
| | 304 | 0 | 0 | 3 | Dead |
| | 307 | 0 | 1 | 3 | Dead |
| | 310 | 0 | 0 | 1 | 1 |
| | 312 | 0 | 1 | 1 | 2 |

Experiment 2: Three of the 30 animals developed signs prior to 1 hr. All 3 were decontaminated with their assigned DC product at the onset of signs, and all died within 5 min after DC. The remaining 27 animals reached the one-hour DC time without exhibiting any signs of intoxication. Each was decontaminated, and the survival results are summarized in Table 9. The 24 hr survival rates were 9/9 (100%), 9/10 (90%) and 6/8 (75%) in the RSDL, the composition and water DC groups, respectively.

TABLE 9

Summary of Survival from Experiment 2

| DC Product | Survival Rate | | | |
|---|---|---|---|---|
| | 2 hr | 4 hr | Next AM | 24 hr |
| RSDL | 9/9 | 9/9 | 9/9 | 9/9 |
| Composition (2%) | 10/10 | 10/10 | 9/10 | 9/10 |
| Water | 8/8 | 8/8 | 6/8 | 6/8 |

Table 10 shows the clinical assessment scores at 2 and 4 hr after DC, the next morning, and at 24 hr after exposure in the subset of animals that were sign-free when DC was performed 1 hr after exposure. Over the course of the post-DC period, 5 of 9 RSDL animals, 6 of 10 composition animals and 6 of 8 water animals displayed signs of nerve agent poisoning of varying severity and time to onset. At 24 hr, none of the RSDL animals had died, one was very severely intoxicated, and 8 of 9 were normal looking. In the composition group, one animal died, two other animals had mild or moderate signs and 7 of 10 were normal looking. The water-decontaminated animals at 24 hr were clearly sicker than the animals in the composition and RSDL groups. Only 2 of 8 animals were normal looking, two had died, two were severely or very severely affected and two had mild to moderate signs.

TABLE 10

Clinical Assessment Scores in Individual Animals at 2 and 4 Hr after DC, the Next Morning and at 24 Hr after Exposure to $10xLD_{50}$ (Experiment 2)

| DC Product | Animal # | Clinical Assessment Scores (CAS) | | | |
|---|---|---|---|---|---|
| | | 2 hr | 4 hr | Next AM | 24 hr |
| RSDL | 318 | 1 | 0 | 0 | 0 |
| | 321 | 0 | 0 | 0 | 0 |
| | 323 | 1 | 0 | 1 | 0 |
| | 327 | 0 | 0 | 0 | 0 |
| | 330 | 0 | 0 | 0 | 0 |
| | 333* | 1 | 0 | 0 | 0 |
| | 336* | 3 | 3 | 4 | 4 |
| | 340* | 0 | 0 | 0 | 0 |
| | 344* | 2 | 2 | 0 | 0 |
| Composition (2%) | 319 | 0 | 0 | 0 | 0 |
| | 324 | 0 | 1 | 1 | 1 |
| | 325 | 0 | 0 | 2 | 2 |
| | 328 | 0 | 0 | 0 | 0 |
| | 331 | 0 | 0 | Dead | Dead |
| | 332* | 0 | 0 | 0 | 0 |
| | 334* | 2 | 0 | 0 | 0 |
| | 335* | 1 | 0 | 0 | 0 |
| | 343* | 0 | 0 | 0 | 0 |
| | 345* | 1 | 0 | 0 | 0 |
| Water | 317 | 0 | 0 | 0 | 0 |
| | 320 | 1 | 1 | Dead | Dead |
| | 322 | 0 | 0 | 2 | 3 |
| | 326 | 0 | 1 | 2 | 1 |
| | 329 | 0 | 0 | 3 | 4 |
| | 337* | 1 | 2 | Dead | Dead |
| | 339* | 0 | 0 | 0 | 0 |
| | 346* | 1 | 2 | 2 | 2 |

Conclusion: RSDL and the composition were both effective in preventing lethality when used 3 hr after dermal application of $5\times LD_{50}$ of this agent in un-anesthetized, fur-clipped animals. Each group had high survival rates at 24 hr. Mild to moderate toxic signs were present in 5/9 RSDL animals and in 4/8 of the composition animals.

The water DC group was included in the study as a control to evaluate the role of physical removal. Survival rate (83%) at 24 hr in the water group was not different from the RSDL and composition animals; however, more of the water-decontaminated animals died, showed signs of intoxication, and were more severely affected the day after exposure.

Example 7

This example analyzed skin decontamination efficacy of the composition and RSDL in guinea pigs following topical VX application, using methods that mimic mass casualty DC procedures Animals: Animal information is the same as in previous studies.

Materials: An aliquot of neat VX was obtained from the USAMRICD Chemical Exclusion Area each exposure day. RSDL sponge pads were purchased in sealed packages from First Line Technology, Chantilly, VA. Bulk RSDL was purchased from Emergent Biosolutions, Rockville, MD. The composition was prepared as a concentrated solution of 9.51% peracid and 17.4% hydrogen peroxide, and aliquots were diluted to a 2% peracid concentration in deionized water each test day.

Agent Exposure: Agent exposure method was the same as in previous VX studies.

Decontamination (DC) Procedure: The exposure site on each animal was decontaminated two minutes after VX application with tap water, 1% Dawn™ dish detergent, RSDL, or 2% composition. A three-step DC procedure designed to mimic procedures employed in a mass casualty chemical agent incident was utilized. In step 1, the DC material was applied by swiping an applicator containing the DC material 10 times quickly in short strokes across the exposure site in a head-to-tail direction; the DC material remained on the skin for 2 min. In step 2, the DC material was removed by wiping the exposure site 5 times quickly in short strokes in a head-to-tail direction with an applicator wetted with 10 ml of water. In step 3 the exposure area was dried with 5 swipes with a dry gauze applicator. Fresh applicators were used for each procedure on each animal. Water, Dawn™, and the composition were applied with fresh gauze applicators for each animal saturated with 10 ml of DC solution, as described in previous experiments. RSDL was applied using either the gauze applicator (RSDL-G) saturated with 10 ml of RSDL or the commercial sponge pad applicator (RSDL-S), as described in previous studies.

Experimental Design: VX dose-lethality curves (DLCs) were generated for all DC materials using a modified stage-wise adaptive dose design. 1 Each stage consisted of a number of agent doses and animals per dose to establish the range of lethality from 0-100% and to define the response relationship in the projected middle (30-70%) of the DLC. A specialized probit analysis program (Battelle, Columbus, Ohio) and SAS NLIN were used on the cumulative results (survival/lethality) after each stage to estimate the LD50 and 95% confidence intervals (CI) and to assess stopping criteria to limit animal use. The stage process continued with additional challenge doses and animals per agent dose until the ratio of the upper 95% CI minus the lower 95% CI (delta or Fieller's limits) divided by two times the MLD estimate from the latest stage was less than 0.4 (stopping criteria) or up to 40 animals were used. After exposure and DC, each animal was monitored continuously for up to 2 hr until the onset of toxic signs appeared, then at 4 hr after DC and again at 24 hr after exposure.

Statistics: A final probit analysis was conducted on all stages from the 24 hr responses for each DC material. The LD50s, LD1, LD10, LD16, LD30, LD70, LD84, LD90, and LD99 with their respective 95% CI were calculated by both Fieller's and delta methods, and the slopes were determined.3,4 A protective ratio (PR), defined as LD50 of VX in animals treated with each DC material divided by the historic LD50 of VX in untreated animals of 140 μg/kg8 in fur-clipped un-anesthetized guinea pigs, was calculated. This estimate was used to compare the effectiveness of the DC treatments using a specialized probit program (Battelle, Columbus, OH) and SAS.

Figure 13:
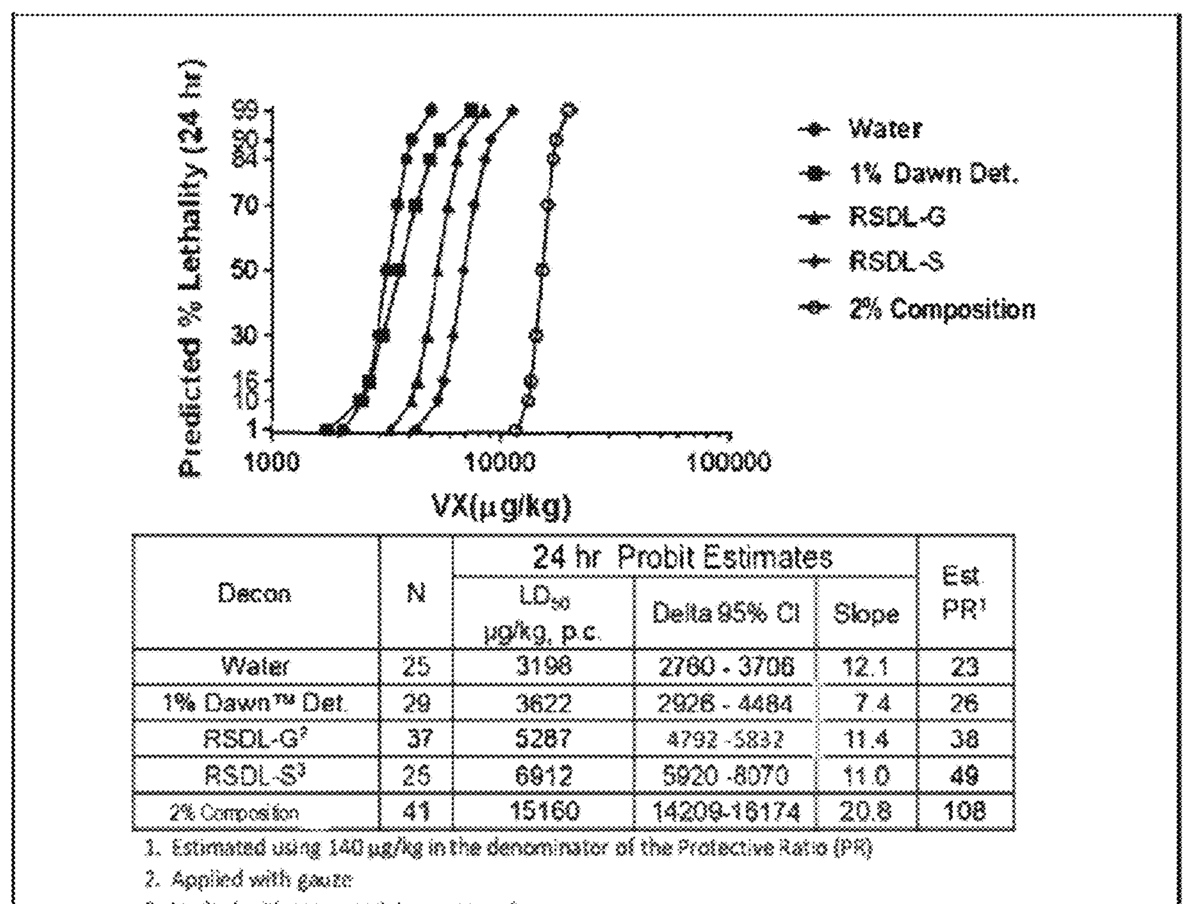
FIG. 13 is a depiction of skin decontamination efficacy of various materials using a 3-step decontamination method mimicking mass casualty procedures, following topical application of VX. The DC was performed 2 min after agent application. The graph shows the probit-predicted dose-lethality curves from 24 hr mortality. The table shows calculated probit estimates for LD50, 95% CI, slope, group sizes, and estimated protective ratios (PR).

Results: FIG. 13 graphs the 24 hr probit-predicted VX dose-lethality curves for skin decontamination at 2 min after agent application with water, 1% Dawn™, RSDL-G, RSDL-S and 2% composition using a 3-step DC procedure as well as the probit estimates at 24 hr for the LD50, 95% CI and slope for each DC material. The composition was significantly more effective than any of the other DC materials, with an estimated PR of 108. The composition was more than 4 times more effective than tap water or soapy water, and more than 2 times more effective than RSDL applied with the commercial sponge pad (RSDL-S) or with the gauze (RSDL-G) applicator. There was a trend suggesting that the RSDL-S was more effective than RSDL-G.

Conclusion: The composition was at least 2-fold more effective than RSDL and 4-to 4.5-fold more effective than tap water or soapy water using a 3-step skin DC methodology that mimics mass DC procedures against topically applied VX in guinea pigs. Since the composition was applied and left on the skin for only 2 min prior to rinsing and drying of the skin, the results suggest that the composition neutralized VX on skin.

Example 8

This example analyzed Skin DC efficacy of the composition and RSDL following topical VX application in swine.

Animals: Gottingen mini-pigs were acclimated to being in a transfer sling and in a cage in a fume hood. Animals were trained to respond to Gatorade, which was used to entice the animal to approach the edge of the cage with its head down so that agent could be applied to the scalp and decontamination solution could be rubbed across the exposure site. On the day of exposure, the animals were weighed, the hair on the scalp was clipped and a 1-inch diameter circle was drawn on the scalp.

Experimental Design: While the animal was being given Gatorade, $2 \times LD_{50}$ (490 μg/kg) of VX was applied using a Hamilton digital syringe to the center of the circle. At either 5 min or 1 hour after VX application, the site was decontaminated with either RSDL or the composition, by wiping the site 3 times with the DC product. Care was taken to ensure that the DC product did not enter the eye by using a piece of dry gauze. The DC product was allowed to stay on the skin for 15 minutes, then removed by wiping the site 3 times with saline-soaked gauze. Animals were observed and kept in the hood for 24 hours, with access to food and water. All surviving animals were euthanized at 24 hours. The exposure area of the scalp was removed and placed in bleach for decontamination.

Conclusion: In this mini-pig model, RSDL and the composition were comparable in decontamination effectiveness.

What is claimed is:

1. A method for wound decontamination after exposure to a chemical biological warfare agent, the method comprising contacting a wound exposed to a chemical biological warfare agent with a therapeutically effective amount of a composition comprising wound healing compounds, wherein the wound healing compounds consist of:

(a) peracetic acid at a concentration of between 0.64 wt. % and 8.64 wt. % based on the total weight of the composition;

(b) acetic acid at a concentration of between 1.2 wt. % and 15.84 wt. % based on the total weight of the composition; and (c) hydrogen peroxide at a concentration of between 1.2 wt. % and 14.4 wt. % based on the total weight of the composition.

2. The method of claim 1, wherein the wound is a surgical wound, battle wound, accidental wound, chemical burn wound, or a chronic wound.

3. The method of claim 1, wherein the wound is contacted with the composition once a day.

4. The method of claim 1, wherein the composition is formulated as a gel, a liquid, lotion, skin patch, irrigation gel, a spray, application granules, or a combination thereof.

5. The method of claim 1, further comprising a magnesium salt.

6. The method of claim 5, wherein the magnesium salt is a magnesium salt of peracetic acid.

* * * * *